(12) United States Patent
Desjardins

(10) Patent No.: US 10,363,015 B2
(45) Date of Patent: Jul. 30, 2019

(54) METHOD AND APPARATUS FOR DETERMINING THE LOCATION OF A MEDICAL INSTRUMENT WITH RESPECT TO ULTRASOUND IMAGING, AND A MEDICAL INSTRUMENT TO FACILITATE SUCH DETERMINATION

(71) Applicant: UCL Business PLC, London (GB)

(72) Inventor: Adrien Desjardins, London (GB)

(73) Assignee: UCL BUSINESS PLC, London (GB)

( * ) Notice: Subject to any disclaimer, the term of this patent is extended or adjusted under 35 U.S.C. 154(b) by 583 days.

(21) Appl. No.: 14/775,566

(22) PCT Filed: Apr. 25, 2014

(86) PCT No.: PCT/GB2014/051286
§ 371 (c)(1),
(2) Date: Sep. 11, 2015

(87) PCT Pub. No.: WO2014/174305
PCT Pub. Date: Oct. 30, 2014

(65) Prior Publication Data
US 2016/0038119 A1    Feb. 11, 2016

(30) Foreign Application Priority Data

Apr. 26, 2013  (GB) .................................. 1307551.0
Feb. 17, 2014  (GB) .................................. 1402759.3

(51) Int. Cl.
*A61B 8/00*     (2006.01)
*A61B 8/14*     (2006.01)
(Continued)

(52) U.S. Cl.
CPC .......... *A61B 8/4477* (2013.01); *A61B 5/0059* (2013.01); *A61B 8/0841* (2013.01);
(Continued)

(58) Field of Classification Search
CPC ........ A61B 17/3403; A61B 2017/3413; A61B 2034/2063; A61B 2090/378;
(Continued)

(56) References Cited

U.S. PATENT DOCUMENTS 5,797,849 A    8/1998  Vesely et al.

FOREIGN PATENT DOCUMENTS

WO    2012172458    12/2012

OTHER PUBLICATIONS

European Patent Office, European supplementary office action Application No. 14 719 836.0-1664, dated Nov. 30, 2017.
(Continued)

*Primary Examiner* — Michael T Rozanski
(74) *Attorney, Agent, or Firm* — Park, Vaughan, Fleming & Dowler LLP

(57) ABSTRACT

An ultrasound system comprises an ultrasound unit including: an ultrasound probe including a first set of imaging transducer elements and a second set of localisation transducer elements. The first set of imaging transducer elements are configured to: (i) produce ultrasound imaging transmissions into the human body, wherein the ultrasound imaging transmissions are focussed into an image scan plane, and (ii) receive reflections of the ultrasound imaging transmissions for generating a two-dimensional anatomical image corresponding to the image scan plane. The second set of localisation transducer elements are configured to produce ultrasound localisation transmissions into the human body for locating the medical instrument with respect to the anatomical image, wherein the ultrasound localisation transmissions extend outside the image scan plane.

20 Claims, 26 Drawing Sheets

(51) Int. Cl.
| | |
|---|---|
| *A61B 8/08* | (2006.01) |
| *A61B 5/00* | (2006.01) |
| *A61B 17/34* | (2006.01) |
| *G01H 9/00* | (2006.01) |
| *G02F 1/125* | (2006.01) |
| *A61B 34/20* | (2016.01) |
| *A61B 90/00* | (2016.01) |

(52) U.S. Cl.
CPC ............. *A61B 8/14* (2013.01); *A61B 8/4416* (2013.01); *A61B 8/4444* (2013.01); *A61B 8/4483* (2013.01); *A61B 8/4488* (2013.01); *A61B 8/4494* (2013.01); *A61B 8/463* (2013.01); *A61B 8/5207* (2013.01); *A61B 17/3403* (2013.01); *A61B 34/20* (2016.02); *G01H 9/004* (2013.01); *G02F 1/125* (2013.01); *A61B 5/0095* (2013.01); *A61B 2017/3413* (2013.01); *A61B 2034/2063* (2016.02); *A61B 2090/378* (2016.02); *A61B 2090/3786* (2016.02)

(58) Field of Classification Search
CPC ............ A61B 2090/3786; A61B 34/20; A61B 5/0059; A61B 5/0095; A61B 8/0841; A61B 8/14; A61B 8/4416; A61B 8/4444; A61B 8/4447; A61B 8/4483; A61B 8/4488; A61B 8/4494; A61B 8/463; A61B 8/5207; G01H 9/004; G02F 1/125
See application file for complete search history.

(56) References Cited

OTHER PUBLICATIONS

Intellectual Property Office, Patents Directorate, Patents Act 1977: Search Report under Section 17(5), dated Jan. 15, 2014 in reference to Application No. GB1307551.0.

METHOD AND APPARATUS FOR DETERMINING THE LOCATION OF A MEDICAL INSTRUMENT WITH RESPECT TO ULTRASOUND IMAGING, AND A MEDICAL INSTRUMENT TO FACILITATE SUCH DETERMINATION

This application claims priority to PCT Application No. PCT/GB2014/051286, filed on 25 Apr. 2014, the contents of which are herein incorporated by reference in their entirety for all purposes.

FIELD OF THE INVENTION

The present invention relates to method and apparatus for determining the location of a medical instrument within a human body with respect to ultrasound imaging of the human body, and to a medical instrument that supports such a determination of location.

BACKGROUND OF THE INVENTION

Ultrasound is widely used to guide the placement of interventional instruments such as needles to targets in the human body. With this imaging modality, it is possible to generate two- and three-dimensional images that provide anatomical information relevant to target identification. A typical ultrasound system can utilize a transducer array to deliver acoustic pulses into the body and to temporally resolve reflected acoustic pulses. A typical ultrasound system provides a two-dimensional image that derives from a scan plane within tissue.

One of the challenges in ultrasound-guided percutaneous interventions is the visualization of a needle tip. During an insertion, the needle tip can readily stray from the image (scan) plane so that its position relative to the ultrasound image is unclear. Reorientation of the imaging transducer of the ultrasound system and/or reinsertion of the needle to bring the tip back into the image plane can be time-consuming and cause patient discomfort.

Another potential problem with locating instruments during ultrasound imaging is that an instrument may have a smooth surface, so that acoustic pulses are specularly reflected from the instrument surface in a direction away from the transducer surface, thereby preventing the instrument from being visible on the ultrasound image. One solution is to use echogenic needles that increase the range of angles at which acoustic pulses are reflected from the needle surface, which may include indentations on the needle cannula and stylet [see, e.g., U.S. Pat. No. 5,490,521] or polymer coatings with microbubbles [see, e.g., US2005-0074406]. Companies that supply needles that have coatings or surface modifications to increase the echogenicity of the needles so that they are more prominent in ultrasound images include Cook Medical (www.cookmedical.com), B Braun (www.bbraun.co.uk) and Pajunk (www.pajunk.com). However, echogenic needs are only visible when they are in the ultrasound imaging plane. In a recent study of needle visibility, commonly-used echogenic needles were not visible on the ultrasound image during 45% of the procedure time [Hebard S and Hocking G. *Reg. Anesth. Pain Med.* 2011; 36:185-189]. Echogenic needles may also introduce large artifacts in ultrasound images that risk obscuring anatomical detail.

Another solution is to mechanically vibrate the instrument so that it can be detected with Doppler ultrasound, as has been suggested for the case of a biopsy needle [see, e.g., U.S. Pat. Nos. 5,095,910 and 5,425,370]. However, this solution again has the limitation that the instrument typically cannot be visualized when it is outside the scan plane.

Commercially available mechanical guides such as those developed by Civco (www.civco.com), or by Bard Access Systems (see www.bardaccess.com) for the Site-Rite® Ultrasound system, mechanically constrain the trajectory of needles. These are generally provided as removable accessories to ultrasound imaging probes, and are designed to limit the direction in which the needle is inserted, so that the needle is maintained close to the scan plane, or at least the needle is more frequently in the ultrasound imaging plane. Accordingly, visibility of the needle in the ultrasound image should be improved. However, once the needle is secured in the mechanical needle guide, approaches to the target cannot be changed without complete withdrawal and reinsertion of the needle. As a result, mechanical needle guides are unsuited to most anaesthesia and interventional pain management procedures, where fine adjustments in needle trajectory and depth are required to achieve adequate local anaesthetic spread around the target nerve. Furthermore, a needle may bend as it passes through tissue, and therefore may still follow a trajectory that lies outside the ultrasound scan plane.

It has also been suggested that the scan plane could be chosen automatically to maximize the visibility of an instrument. For example, U.S. Pat. No. 6,524,247 discloses that the ultrasound beam could be adaptively tilted, while U.S. Pat. No. 6,764,449 discloses that two-dimensional images could automatically be extracted from three-dimensional image volumes in such a way that the needle visibility is maximized However, these two approaches both have the disadvantage that they are typically dependent on robust, real-time segmentation of images to identify instruments. Similarly, devices from Sonosite (www.sonosite.com) use software enhancements of an ultrasound imaging system to implement image processing and beam steering techniques in order to increase the visibility of needles. Again however, these enhancements are only relevant when a needle is the ultrasound imaging plane. Furthermore, the positions of needle tips in the body are not explicitly determined, and it is also difficult to use this approach with devices having low echogenicity such as catheters.

Another challenge associated with locating an instrument during ultrasound imaging is that there can be a very low difference between the acoustic impedance of the instrument and the tissue surrounding the instrument. One solution to this problem is based on photoacoustic time-of-flight localization. For example, U.S. Pat. No. 7,068,867 discloses a system in which acoustic waves are generated by the instrument or in tissue adjacent to the instrument by means of the delivery of pulsed light and the photoacoustic effect. In this system, acoustic waves generated by the absorption of pulsed light are received by the ultrasound imaging transducer, and time-of-flight measurements then allow for instrument localization However, the lasers that are currently employed in such a system are expensive. Furthermore, having lasers deliver pulsed light out of instruments may be problematic with respect to eye safety in a clinical environment.

Instrument localization can also be performed with markers positioned on the instrument that are tracked by external sensors, for example, by optical and/or electromagnetic (EM) tracking [see, e.g., Glossop et al., The Journal of Bone and Joint Surgery, 91:23-28 (2009)]. Similarly, Ultrasonix and GE provide EM tracking, whereby sensors in the needle and ultrasound imaging probe are tracked by an external field generator that is positioned close to the patient. However, such sensors are generally expensive and are currently not disposable. Furthermore, the external field generator is typically bulky, likewise the sensors are typically bulky (and may therefore be incompatible with small needles). In addition, marker-based localization systems may involve long set-up times and calibration procedures, such as to integrate a non-disposable sensor into a disposable needle component, which makes them unattractive for short procedures. In addition, such systems may be sensitive to subtle changes in the external environment, for example, the introduction of metal objects (e.g. a surgical tool) that alter EM fields in the case of EM tracking and greatly reduce tracking accuracy, or opaque objects that affect line-of-sight in the case of optical tracking.

Various techniques have been proposed to identify the position of a medical needle during percutaneous interventions by receiving acoustic waves generated by the imaging transducer with a second transducer integrated into the needle. U.S. Pat. No. 5,158,088 proposes that a transducer positioned at the needle tip could receive acoustic pulses transmitted by an imaging transducer, thereby allowing for an alert to be provided to the physician when the needle tip is in the scan plane. This device has the limitation that it generally does not provide information about the position of the needle tip when the needle tip is not in the scan plane. U.S. Pat. No. 4,249,539 and U.S. Pat. No. 5,161,536 propose that needle tip localization is performed by measuring the time-of-flight of individual spatially-focused acoustic pulses delivered from an imaging transducer to a second transducer positioned at the needle tip. In the case of U.S. Pat. No. 4,249,539 the needle transducer confirms receipt of the ultrasound pulse by transmitting its own ultrasound pulse back to the imaging transducer. However, such an approach has the disadvantage that acoustic pulses from the imaging transducer are typically only received by the needle transducer when the needle tip intersects the scan plane. Nikolov and Jansen have demonstrated needle localization in two and three dimensions with time-of-flight measurements of individual unfocused acoustic pulses [see, e.g., J. Nikolov and J. Jansen, Ultrasonics Symposium, 2008. IUS 2008. IEEE, pp. 479-482 (2008)]. This publication describes a proposed transmission of a single pulse and subsequent reception of said pulse, followed by transmission of a second single pulse and subsequent reception of said pulse, and so on. One significant disadvantage of this solution is that the process of emitting and receiving a large number of individual pulses, which the authors suggest is useful for reducing errors, could be very time-consuming. A second disadvantage is that it involves an ultrasound imaging probe which is capable of providing three-dimensional ultrasound images—however, such devices are currently bulky and prohibitively expensive for many ultrasound-guided procedures. WO 2011/138698, U.S. Pat. No. 6,587,709 and WO 2012/066437 also disclose medical device tracking based on transmission of acoustic pulses between a catheter and a 3D imaging transducer. However, these proposals are also dependent on the presence of an ultrasound imaging probe that is capable of providing three-dimensional ultrasound images, whereas this type of probe is not available for a wide range of medical procedures.

WO 98/39669 discloses an ultrasound imaging head having a window through which ultrasound is transmitted and received by an image transducer. The imaging head also holds three or more position transducers that form a plane perpendicular to the ultrasound imaging beam. There are also reference transducers mounted to the patient's body. The orientation of the imaging plane with respect to the coordinate system defined by the reference transducers can be calculated by determining the location of the position transducers on the imaging head. This then allows a real-time imaging output to display in three-dimensions the position of an instrument relative to the ultrasound imaging plane.

Despite the range of existing solutions discussed above, the problem of accurately and consistently locating instruments during ultrasound imaging in a manner that is compatible with most clinical procedures remains Consequently, procedures may involve multiple instrument insertions that increase patient discomfort and procedure duration, and may result in additional risks such as the inadvertent penetration of an important tissue structure when the position of the instrument tip is not known. Accordingly, there is a significant need for a system that can determine the position of an instrument accurately and in real-time, with minimal compromise to scanning speed.

SUMMARY OF THE INVENTION

The invention is defined in the appended claims.

An ultrasound system is provided comprising an ultrasound unit including an ultrasound probe as described herein for producing ultrasound localisation transmissions into a human body. The ultrasound localisation transmissions are received by the transducer in a medical instrument. The ultrasound system further comprises a sensor console for receiving the signals from the transducer that correspond to localisation transmissions. The received signals are processed by the ultrasound system to determine the location of the medical instrument within the human body relative to the ultrasound probe.

An ultrasound probe is provided for acquiring an anatomical image of a human body and for locating a medical instrument with respect to the image. The ultrasound probe includes a first set of imaging transducer elements and a second set of localisation transducer elements. The first set of imaging transducer elements are distinct and disjoint from the second set of localisation transducer elements. The first set of imaging transducer elements are configured to: (i) produce ultrasound imaging transmissions into the human body, wherein the ultrasound imaging transmissions are focussed into an image scan plane, and (ii) receive reflections of the ultrasound imaging transmissions for generating a two-dimensional anatomical image corresponding to the image scan plane. The second set of localisation transducer elements are configured to produce ultrasound localisation transmissions into the human body for locating the medical instrument with respect to the anatomical image. The ultrasound localisation transmissions extend outside the image scan plane. At least two transducer elements from said second set are spaced from one other in a direction perpendicular to the image scan plane.

A medical instrument is provided having a needle-like shape for insertion into a human body. The instrument comprises: an elongated structure forming the needle-like shape and having a bevelled surface at its distal tip; at least one optical fiber, running along the elongated structure, for transmitting an interrogation light signal to the distal tip and for transmitting a data signal back from the distal tip or side aperture; and a transducer located at the distal tip for detecting ultrasound transmissions incident upon the distal tip. The transducer includes at least one surface to reflect the interrogation light signal from the optical fiber with an intensity and/or phase that varies according to the incident ultrasound transmissions to generate said data signal. The transducer does not extend beyond said bevelled surface.

In some embodiments, the at least one reflective surface to reflect the interrogation light signal is dichroic so as to be substantially reflective for light having a first wavelength range and substantially transmissive for light having a second wavelength range which is different from the first wavelength range. The interrogation light signal falls substantially within the first wavelength range. Light within the second wavelength range may be transmitted and/or received along the optical fibre (concurrently with the use of the interrogation light for detecting the data signal). The light within the second wavelength may be used, for example, for performing spectroscopy, photoacoustic stimulation, or optical ablation in (of) tissue in the human body.

Also provided is a method of using an ultrasound probe for acquiring an anatomical image of a human body and for locating a medical instrument with respect to said image, the ultrasound probe including a first set of imaging transducer elements and a second set of localisation transducer elements, wherein the first set of imaging transducer elements are distinct and disjoint from the second set of localisation transducer elements. The method comprises the first set of imaging transducer elements producing ultrasound imaging transmissions into the human body, wherein the ultrasound imaging transmissions are focussed into an image scan plane, and receiving reflections of the ultrasound imaging transmissions for generating a two-dimensional anatomical image corresponding to the image scan plane; and the second set of localisation transducer elements producing ultrasound localisation transmissions into the human body for locating the medical instrument with respect to the anatomical image, wherein the ultrasound localisation transmissions extend outside the image scan plane. At least two transducer elements from said second set are spaced from one other in a direction perpendicular to the image scan plane.

Such a method may further comprise receiving said ultrasound localisation transmissions by a transducer in the medical instrument; receiving by a sensor console the signals from said transducer that correspond to localisation transmissions; and processing the received signals to determine the location of the medical instrument within the human body relative to the ultrasound probe.

It will be appreciated that these methods may benefit from the same features and enhancements as described above in relation to the embodiments of the ultrasound probe and medical instrument.

Also provided is an ultrasound probe for acquiring an anatomical image of a human body and for locating a medical instrument with respect to said image, the ultrasound probe including a first set of imaging transducer elements and a second set of localisation transducer elements, wherein the first set of imaging transducer elements are distinct and disjoint from the second set of localisation transducer elements. The first set of imaging transducer elements are configured to: (i) produce ultrasound imaging transmissions into the human body, wherein the ultrasound imaging transmissions are focussed into an image scan plane, and (ii) receive reflections of the ultrasound imaging transmissions for generating a two-dimensional anatomical image corresponding to the image scan plane. The second set of localisation transducer elements are configured to receive ultrasound localisation transmissions for locating the medical instrument with respect to the anatomical image, wherein the ultrasound localisation transmissions are produced by the medical instrument and travel to the localisation transducer elements through the human body. At least two transducer elements from said second set are spaced from one other in a direction perpendicular to the image scan plane so as to receive the ultrasound localisation transmissions from spatial regions of the human body which extend beyond the image scan plane.

Also provided is a method of operating an ultrasound probe for acquiring an anatomical image of a human body and for locating a medical instrument with respect to said image, the ultrasound probe including a first set of imaging transducer elements and a second set of localisation transducer elements, wherein the first set of imaging transducer elements are distinct and disjoint from the second set of localisation transducer elements. The method comprises the first set of imaging transducer elements producing ultrasound imaging transmissions into the human body, wherein the ultrasound imaging transmissions are focussed into an image scan plane, and receiving reflections of the ultrasound imaging transmissions for generating a two-dimensional anatomical image corresponding to the image scan plane; and the second set of localisation transducer elements receiving ultrasound localisation transmissions for locating the medical instrument with respect to the anatomical image, wherein the ultrasound localisation transmissions are produced by the medical instrument and travel to the localisation transducer elements through the human body. At least two transducer elements from said second set are spaced from one other in a direction perpendicular to the image scan plane so as to receive the ultrasound localisation transmissions from spatial regions of the human body which extend beyond the image scan plane.

In such a method, there is an ultrasound unit that includes said ultrasound probe which receives said ultrasound localisation transmissions, and the method further comprises a sensor console receiving signals from said ultrasound unit that correspond to the localisation transmissions; and processing the received signals to determine the location of the medical instrument within the human body relative to the ultrasound probe.

Again, it will be appreciated that these methods may benefit from the same features and enhancements as described above in relation to the embodiments of the ultrasound probe and medical instrument. In addition, it will be appreciated that the various medical instruments, needles, etc., described herein can be used in conjunction with any of the ultrasound probes as described herein, as appropriate, to acquire an anatomical image of a human body and to locate the medical instrument with respect to said image.

BRIEF DESCRIPTION OF DRAWINGS

Various embodiments of the invention will now be described in detail by way of example only with reference to the following drawings:

FIG. 18A is a transverse cross-section and FIG. 18B is a longitudinal cross-section.

FIG. 19A is a transverse cross-section and FIG. 19B is a longitudinal cross-section.

FIG. 20A is a transverse cross-section and FIG. 20B is a longitudinal cross-section.

DETAILED DESCRIPTION

Figure 1:
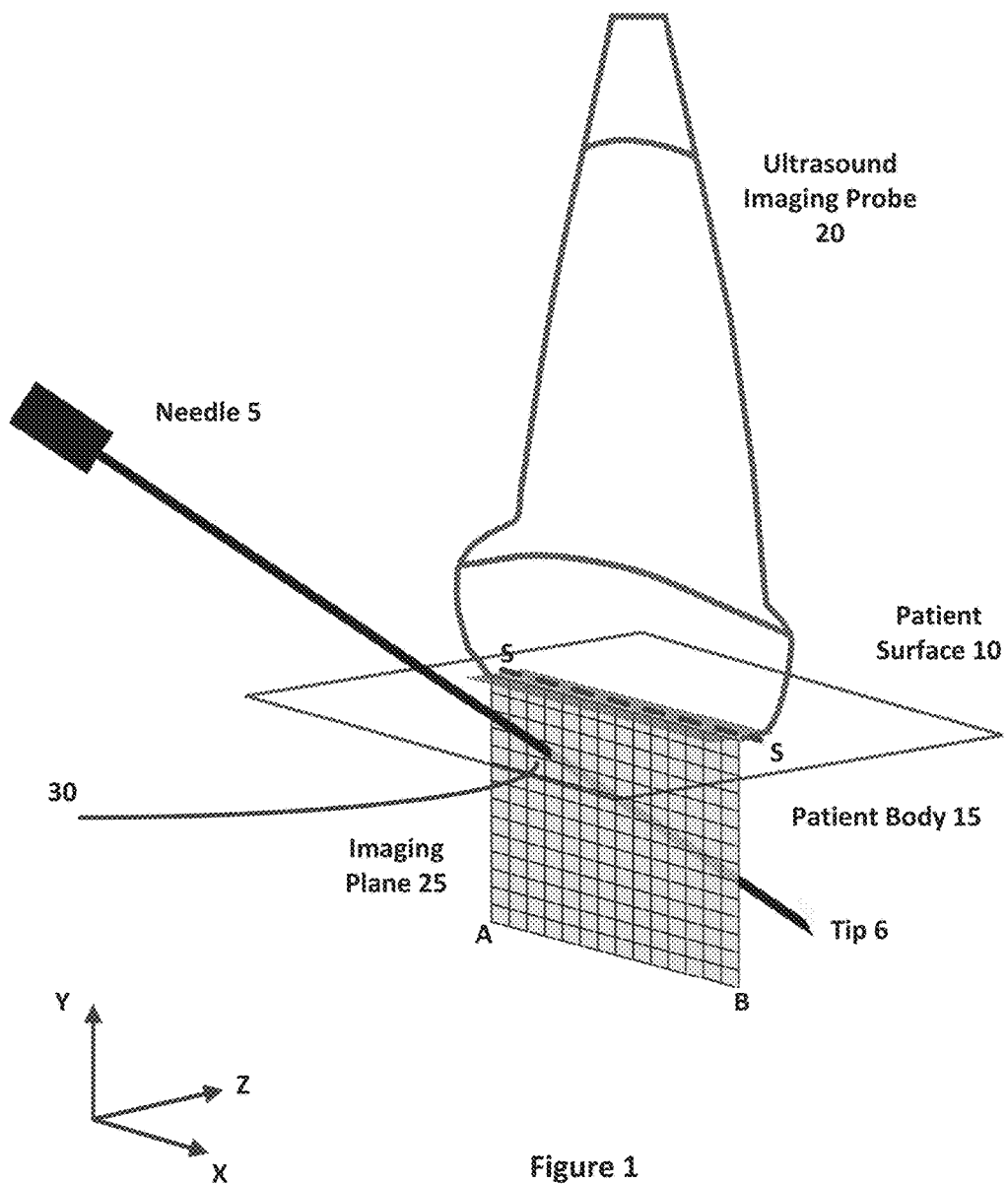
FIG. 1 is a schematic illustration of a conventional procedure using an ultrasound probe to provide imaging to assist in guiding a medical instrument.

Accurately and efficiently guiding a medical device (e.g. a needle or catheter) to a target in the human body is of great importance in a wide range of minimally invasive procedures including peripheral nerve blocks (including an estimated 8 million brachial plexus blocks per year worldwide) and central venous catheterisations (approximately 10 million procedures per year worldwide). Ultrasound imaging, such as shown in FIG. 1, is commonly used for this guidance. Thus in a typical ultrasound-guided procedure, in which a needle is inserted into the human body, an image of the patient anatomy is obtained from a two-dimensional imaging (scan) plane. During peripheral nerve blocks, the interventional target is the region immediately surrounding a nerve.

More particularly, FIG. 1 shows a needle 5 inserted through the patient surface (skin) 10 into the patient body 15. At the same time, an ultrasonic (ultrasound) imaging probe 20 is applied to the patient surface. This probe includes multiple transducer elements arranged substantially along dashed line S-S for producing ultrasound transmissions. The ultrasound imaging probe 20 further includes multiple acoustic sensors, also arranged along the axis S-S (the acoustic sensors may be implemented as part of the transducer elements used to generate the ultrasound transmissions, or may be separate from the transducer elements). The ultrasound probe 20 emits an acoustic signal which penetrates into the patient body 15. Reflections of this acoustic signal from various internal structures within the patient body 15 are then received by the sensors of the probe 20.

More particularly, a conventional ultrasound probe typically produces a tightly focussed ultrasound beam that is repeatedly (and quickly) scanned across an image plane 25, e.g. from A to B and back again. For each beam direction within the image scan plane 25, a pulse is emitted and a set of reflections are received back at the ultrasound probe 20. The timings of the different reflections correspond to the depth of structures within the human body, since the ultrasound signal for reflections from structures deeper within the body takes longer to travel to and then return back from such structures. As this timing information is collected for multiple different beam directions within the image scan plane 25, a 2-dimensional image of imaging plane 25 is achieved—in effect a section through the patient body 15.

Typically, each transmission from the ultrasound probe 20 therefore consists of a single pulse that is focused at a different point within the image scan plane 25. This pulse is generated by multiple transducing elements within an array of imaging transducing elements in the ultrasound probe 20. In other implementations, the imaging transmissions may be formed of several pulses that are focussed at different locations simultaneously (this is known as multiple line transmission). The focussing of these imaging transmissions may be performed electronically and/or with an acoustic lens.

FIG. 1 shows X-Y-Z axes, where the X axis is parallel to the line S-S along the patient surface 10. The Y-axis is perpendicular to the X axis and together they define the image scan plane 25—i.e. the X-Y place is coincident with the imaging plane 25. The Z axis is then perpendicular to both the X axis and the Y axis. In FIG. 1, the Y axis is also substantially perpendicular to the patient surface 10. However, this is not necessarily the case, since an operator is able to tilt the ultrasound probe 20—in effect, rotating the probe about the X axis, in particular, about the line S-S, in order to maintain contact with the patient surface 10; the image plane 25 then rotates likewise about line S-S. We will assume that in such a situation the X-Y-Z coordinate system also rotates in this manner, so the X-Y plane therefore remains coincident with the image scan plane 25. This definition of the X-Y-Z axes will be used throughout the present application.

As noted above, the ultrasound imaging transmissions from the probe 20 are focussed within the image plane 25, hence the configuration shown in FIG. 1 generally does not provide any imaging or sensing outside the image plane 25. It is possible for an operator to change the positioning of the image plane with respect to the patient body, i.e. to image portions of the body that are not currently imaged, by one or more of the following manipulations: (i) moving (translating) the position of the ultrasound probe 20 over the patient surface 10 in a direction perpendicular to line S-S (i.e. parallel to the Z axis); (ii) rotating the ultrasound probe about an axis perpendicular to the patient surface 10 (i.e. about the Y axis); and/or (iii) rotating (tilting) the ultrasound probe about the line S-S, as discussed above. (Note that it is not possible to perform manipulations (ii) and (iii) simultaneously, since most of the ultrasound probe 20 would then lose contact with the patient skin 10, at least for the case where the patient skin is essentially a flat (planar) surface, such as shown in FIG. 1).

Ultrasound imaging as so far described is widely used in a variety of medical investigations and procedures. Significant advantages of ultrasound imaging include immediate (real-time), non-invasive imaging, the absence of potentially dangerous radiation (when compared with X-rays), and small, relatively inexpensive and portable apparatus (when compared with MRI).

One particular use of ultrasound imaging is to provide a real-time indication to a physician of the position of a medical instrument within the patient body 15. This indication can then be used to guide the medical instrument to a desired destination and/or to ensure that the medical instrument avoids unintended damage to other parts of the patient body 15. This situation is also illustrated in FIG. 1, which depicts a needle 5 as a medical instrument inserted into the patient body 15. In most cases, it is important for the physician to be particularly aware of the location of the tip 6 of the needle 5 within the patient body. One reason for this is that the tip 6 of the needle generally represents the specific location where the relevant medical procedure is being performed, and it is important to confirm that this is occurring at the correct position with the patient body. Furthermore, the tip 6 of the needle also presents the greatest risk for causing accidental damage to the patient (for example, by unintentionally puncturing a membrane), and such risk can be reduced by ensuring that the exact current position of the tip of the needle is readily apparent to the physician.

Unfortunately, determining the position of the tip of a medical device or instrument during an ultrasound-guided procedure can be challenging, even for experienced physicians There are two main reasons why this is so:

a) the tip 6 of the needle 5 or other medical device may not be within the two-dimensional ultrasound imaging plane 25 (as is the case in FIG. 1);

b) even if the tip 6 is located within the imaging plane 25, the needle 5 or other medical device may still not give rise to reflections that are apparent on the ultrasound imaging device. Consequently, the tip 6 may then be invisible in the ultrasound image (or at least difficult to see). Note that this lack of ultrasound reflectivity tends to be most severe if the needle is inserted in a direction that is directly away from the ultrasound probe—i.e. within the imaging plane 25, but perpendicular to the line S-S of acoustic sensors (in effect, straight down in the configuration illustrated in FIG. 1, perpendicular to the patient surface 10 and parallel to the Y axis), since in this case the tip 6 is hidden to a certain extent by the rest of the needle 5).

In ideal conditions, the entirety of the needle 5 is within the imaging plane 25 and the tip 6 is clearly visible, for example, because the needle is obliquely angled with respect to the patient surface 10. In practice, however, the probe is often misaligned and the needle intersects the imaging plane at an angle (as illustrated in FIG. 1), so that only a small cross-sectional portion of the needle is visible at the location 30 where the needle 5 intersects the imaging plane 25. In such circumstances, the position of the distal tip 6 is unknown from the image provided by the ultrasound probe 20. This uncertainty of position increases the risk of life-threatening complications, as well as elevating costs by lengthening procedural times.

Figure 1A:
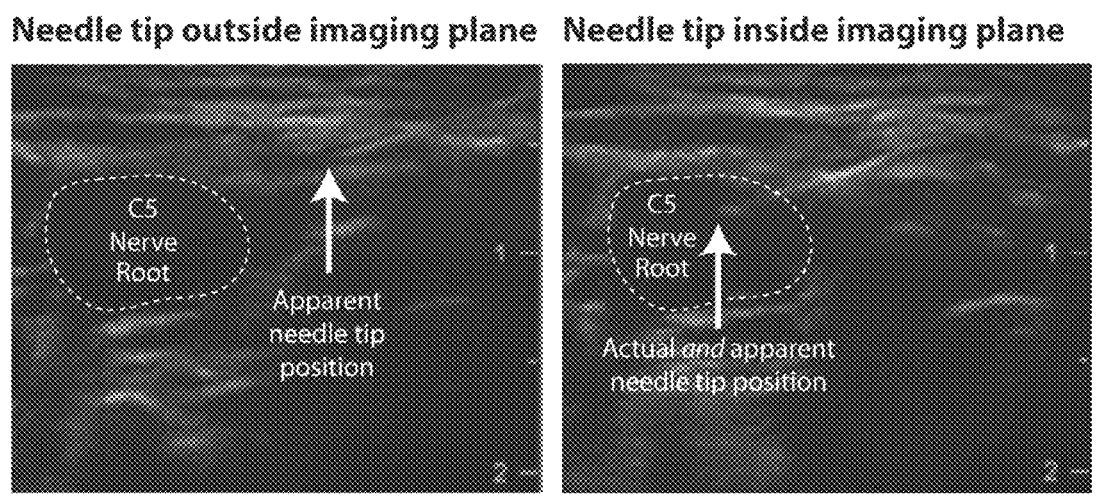
FIG. 1A provides two examples of the ultrasound images produces using the procedure illustrated in FIG. 1 for when the medical instrument is inside and outside the image scan plane.

This situation is illustrated by the two ultrasound images of FIG. 1A. In the left-hand image of FIG. 1A, a needle tip is located outside the image plane 25—as for the configuration of FIG. 1. In this case, the needle tip might be considered, from the scan image alone, to be located at the position shown by the arrow. However, this location actually marks the position where the needle leaves the imaging plane, corresponding to intersection 30 in FIG. 1. In contrast, the right-hand image of FIG. 1A illustrates a situation where the needle tip is located inside the image plane 25. In this configuration, the end of needle is shown correctly in the ultrasound image. It will be appreciated that the two images of FIG. 1A look generally similar, and hence it is difficult for a physician to determine whether an apparent end of a needle or other instrument in a scanned image represents a true position of the needle tip (as for the right hand image), or just the site where the needle leaves the imaging plane (as for the left hand image). This makes it difficult to be certain of the true position of the needle tip in any situation, i.e. irrespective of whether the needle tip is located inside or outside the image scan plane.

As described herein, ultrasonic device tracking (UDT) can be used to help overcome such problems, and to allow for the accurate determination of the position of a medical device in the human body during an ultrasound-guided procedure. With UDT, a very small acoustic sensor is integrated into the tip of a medical device, such as a needle or catheter. As the device 5 is inserted into the body, the acoustic sensor receives transmissions from different elements of the ultrasound imaging probe which is located at surface of the patient. A small console receives signals from the acoustic sensor and processes them to determine the position of the device. In a broadly similar way to the position determination by a GPS receiver based on electromagnetic signals from satellites, the position of the medical device tip may be determined continuously by processing acoustic signals from different elements of the ultrasound imaging probe. This then allows the position of the medical device to be determined and shown on an ultrasound imaging display in real-time.

As described below, UDT typically encompasses modifications to a clinical ultrasound imaging system to include additional ultrasound transmission elements on the imaging probe, and the provision of signal transmission protocols for communicating with the acoustic sensor in the medical device. UDT further encompasses the integration of one or more highly sensitive, inexpensive ultrasound sensors into a medical device, such as a needle or catheter.

Figure 2:
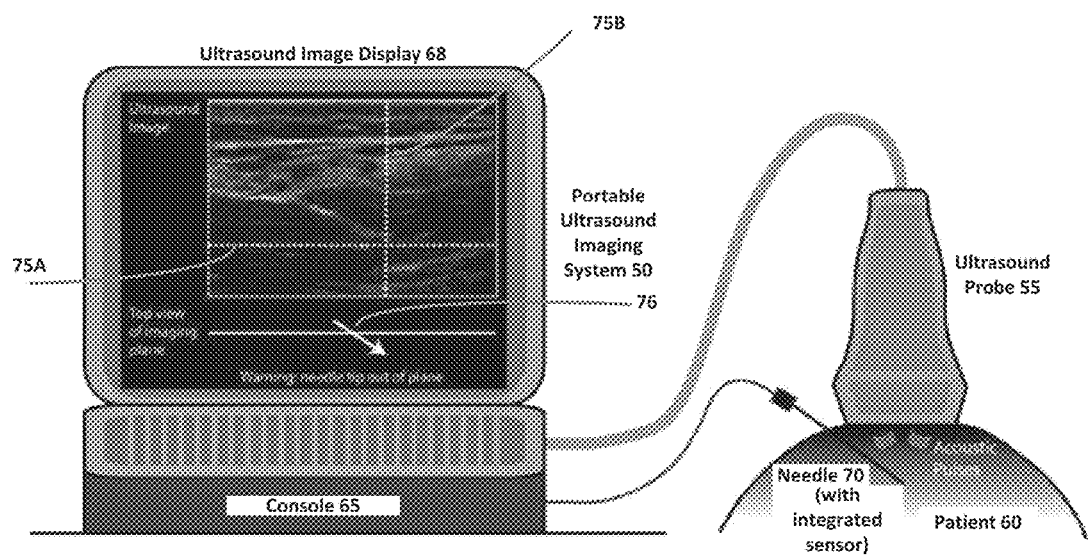
FIG. 2 is a schematic illustration of using an ultrasound probe to provide imaging to assist in guiding a medical instrument in accordance with one embodiment of the invention.

FIG. 2 is a schematic diagram showing an implementation of a system for UDT in accordance with one embodiment of the invention. The three main components are a portable ultrasound imaging system 50, including a console 65 and real-time ultrasound image display 68, a corresponding handheld imaging probe 55 positioned at the surface of the patient 60, and a needle or other medical device 70 to be inserted to its target location in the patient 60. The ultrasound probe 55 and the needle 70 are modified in comparison with the versions shown in FIG. 1. Thus in one embodiment, the needle 70 includes a small acoustic sensor (not shown in FIG. 2), which is integrated into the needle tip. The acoustic sensor is a hydrophone for receiving acoustic waves in an aqueous environment, i.e. within the body of patient 60. Acoustic transmissions (pulses) emitted by the handheld ultrasound imaging probe 55 are detected by the acoustic sensor integrated into the needle, and these detected signals (or information about them) is passed back to the console 65 by wiring that is included within the needle or other medical device 70. The console 65 measures the time taken for various acoustic transmissions to reach the sensor from the ultrasound probe 55, and thereby determines the position of the needle tip relative to the ultrasound imaging plane. This then allows position information to be shown in real-time on the ultrasound imaging system display 68.

In the embodiment of FIG. 2, the same console 65 is used to operate both the ultrasound imaging system and also the needle and acoustic sensor plus associated location system. In other embodiments, separate (physically distinct) consoles may be used for the ultrasound system and the acoustic sensor, with appropriate data communications support between them, for example, electrical, wireless and/or optical data communications. These data communications may be used to transmit information such as a trigger signal from the sensor console to the ultrasound console to cause a localisation ultrasound transmission to take place, or from the ultrasound console to the sensor console to indicate that a localisation ultrasound transmission has just occurred. The data communications may also include timing or positioning information from the sensor console to allow the ultrasound system display 68 to show the most recently detected position of the medical instrument 70.

A data communications link, such as a cable or wireless connection, may be provided between the sensor console (and/or the needle transducer 123) and the ultrasound probe 55. For example, signals from the sensor console may be sent to the ultrasound probe for digitisation by the analog-to-digital (ADC) converters that are present in a conventional ultrasound system for ultrasound imaging. In some cases, these signals may be sent first from the sensor console to the ultrasound probe 55, and then transmitted for analysis to the ultrasound console along the main data channels of the ultrasound system (which are also used for processing the imaging transmissions). The analog signals from the sensor console may be digitised simultaneously by several ADC units having different gain settings.

Where the sensor console and the ultrasound console are separate devices, it is helpful (although not essential) that they have synchronised clocks to support time-of-flight calculations with respect to a signal from the ultrasound probe 55 to the instrument transducer 123. This synchronisation may be performed bilaterally via some appropriate communications protocol, or by mutual synchronisation to an external timing signal. In some embodiments, the synchronisation may allow a conversion from the time base of one console to the time base of the other console, without requiring any formal inter-locking of their respective clocks. The synchronisation allows, for example, the ultrasound system to provide information about the sequence of clock times at (or between) which localisation transmissions were performed.

In FIG. 2, the depth and lateral position of the needle 70 within the image scan plane 25 are indicated by dashed lines 75A, 75B respectively on the ultrasound image, while the direction of the needle tip and the distance of the needle tip from the image scan plane 25 are indicated directly below with an arrow 76. It will be appreciated that the precise format of the display of the needle position and direction on image display 68 may be varied, for example, depending on the type of procedure and the preferences of any particular physician.

Figure 3:
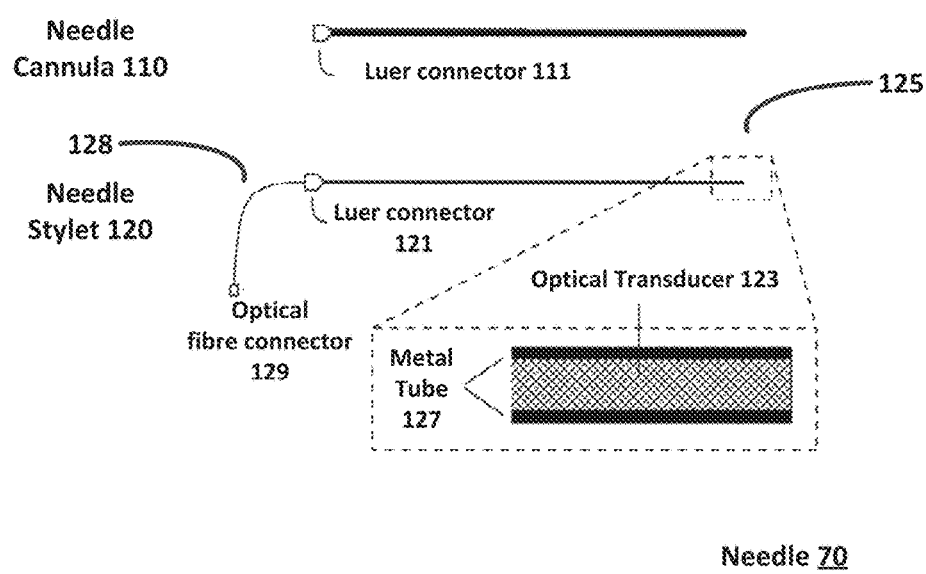
FIG. 3 is a schematic illustration of the medical instrument used in FIG. 2 in accordance with one embodiment of the invention.

FIG. 3 illustrates a needle 70 in accordance with one embodiment of the invention. As is common for existing needles, the needle shown in FIG. 3 comprises two parts: a cannula 110 and a stylet 120. The cannula 110 is generally in the form of a hollow tube, for injecting a fluid. The stylet is generally a thin, solid structure that fits inside the cannula to prevent tissue entering the cannula when the cannula is being inserted into a patient body. The cannula 110 and the stylet are both provided with luer connectors, 111 and 121 respectively, to facilitate connecting the cannula to the stylet or to other medical devices such as a syringe instead of the stylet. A transducer 123 is located at the tip 125 of the needle stylet 120. The end of the needle may further include an acoustic scattering medium (not shown) to help incoming ultrasound transmissions impinge on the transducer 123, and/or an acoustically transparent protective coating (not shown) formed over the transducer 123 (and the acoustic scattering medium if provided).

The transducer 123 has a diameter equal to that of a single-mode optical fiber, and is substantially uniform (omni-directional) in terms of sensitivity across a frequency range of about 1 to 50 MHz. An example of one such transducer 123 is described in P. Beard, et al., IEEE Transactions on Ultrasonics, Ferroelectrics, and Frequency Control, vol. 47(1): 256-264 (2000). The transducer described by Beard et al. includes a single-mode fiber and a polymer coating at the distal end that is interrogated by laser light coupled into the single mode fiber; reflected light is received by a photodetector that generates an electrical signal Ultrasound emissions from an imaging transducer (such as ultrasound imaging probe 55 in FIG. 2) can directly impinge on the instrument transducer 123, or they may reflect first off parts of the cannula 110 and/or stylet 120 prior to impinging on the instrument transducer 123.

Various techniques may be used for integrating the transducer 123 into the stylet 120. For example, the transducer 123 may be enclosed in a thin metal tube 127 and a standard luer connector 121 placed at the proximal end so that the instrument is compatible with the needle cannula 110. The optical fiber 128 from the transducer 123 passes along the inside of the thin metal tube 127, exits via a hole in the luer connector 121, and then terminates at an optical fiber connector 129. Another possible arrangement (not shown in FIG. 3) is that the instrument transducer 123 is combined with the needle 70 by incorporating the transducer within a flexible sheath that is wrapped around a portion of the needle 70 (or other medical instrument). Note that at the proximal end of the needle 70, the optical fiber 128 may pass along the same tube as used to provide fluids (e.g. injections) into the needle 70. This reduces clutter in the vicinity of a patient, and hence helps to reduce the risk that the optical fiber 128 is accidentally damaged or disconnected.

In another implementation, the instrument transducer 123 may comprise a piezoelectric transducer. In this case, the connection between the needle 70 (or other form of instrument) and the ultrasound imaging console may comprise some form of wiring and electronic circuitry to relay electrical signals from the piezoelectric element to a receiver in the console. It is also possible to have some form of wireless link from the needle 70 to a receiving console. The needle may also be provided with a light guide—this can deliver a visible indication that the transducer 123 is connected to the console 65.

The tip of needle 70 may be provided with echogenic enhancements, for example on the inner surface of the cannula. These enhancements may comprise grooves, abrasions or similar, and can be used to help ensure that the transducer 123 receives the ultrasonic transmissions from probe 55, irrespective of the particular angle of the needle 70 with respect to the direction of the ultrasonic transmissions.

Figure 4:
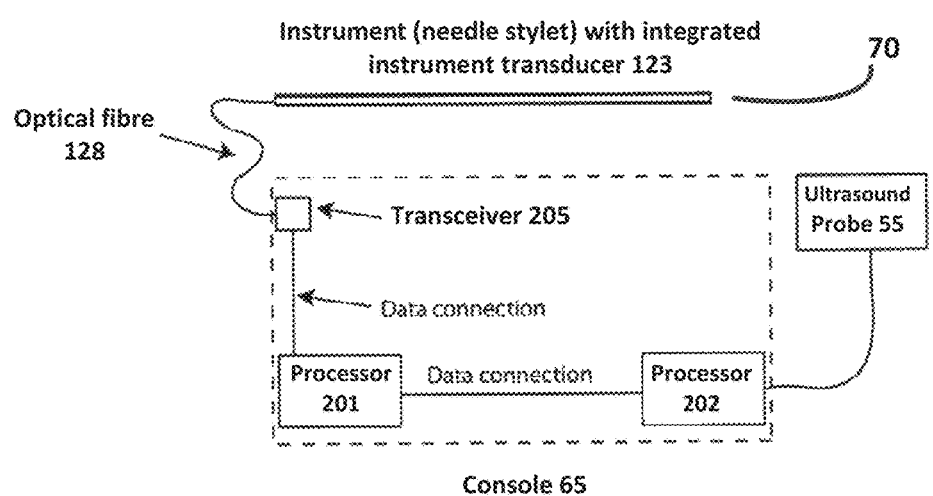
FIG. 4 is a schematic illustration showing the configuration of data processing facilities used in FIG. 2 in accordance with one embodiment of the invention.

FIG. 4 illustrates the combination of the needle 70 and transducer 123 with the console 65 in accordance with one embodiment of the invention. In particular, optical fiber 128 is connected to a transceiver 205 located in the console 65. The console is provided with two processors, a first processor 201 connected to the transceiver 205 for receiving and processing the signals from transducer 123, and a second processor 202 connected to the ultrasound probe 55 for receiving and processing the ultrasound image. The two processors 201 and 202 are linked by a data bus or other appropriate form of data connection. Note that depending on the particular implementation, each of the first and second processors may be implemented by a group of one or more processors; alternatively, the first and second processors may be implemented jointly by a single processor (or a single group of processors). In addition, as noted above, separate consoles may be provided for receiving and processing the signals from transducer 123 and from ultrasound probe 55. In any event, the one or more consoles may be configured so that acquisition and processing of the signals from the instrument transducer 123 are synchronized to the transmission and reception of acoustic energy by the ultrasound probe 55. The ultrasound probe 55 is configured to produce two types of ultrasound transmissions, whereby a "transmission" generally represents ultrasound waves generated by the imaging transducer, e.g. for a time period during which the transducer elements of the ultrasound probe that generate the ultrasound waves are continuously in transmit mode. The two types of acoustic transmission comprise: (a) transmissions for obtaining anatomical images, which are focussed into the scan plane, are referred to herein as "imaging transmissions"; and (b) transmissions which are weakly focussed or unfocussed (or focussed out of the scan plane) for performing instrument localisation are referred to herein as "localisation transmissions". For each of the imaging transmissions and the localisation transmissions, the focussing may be performed electronically and/or mechanically.

Figure 5:
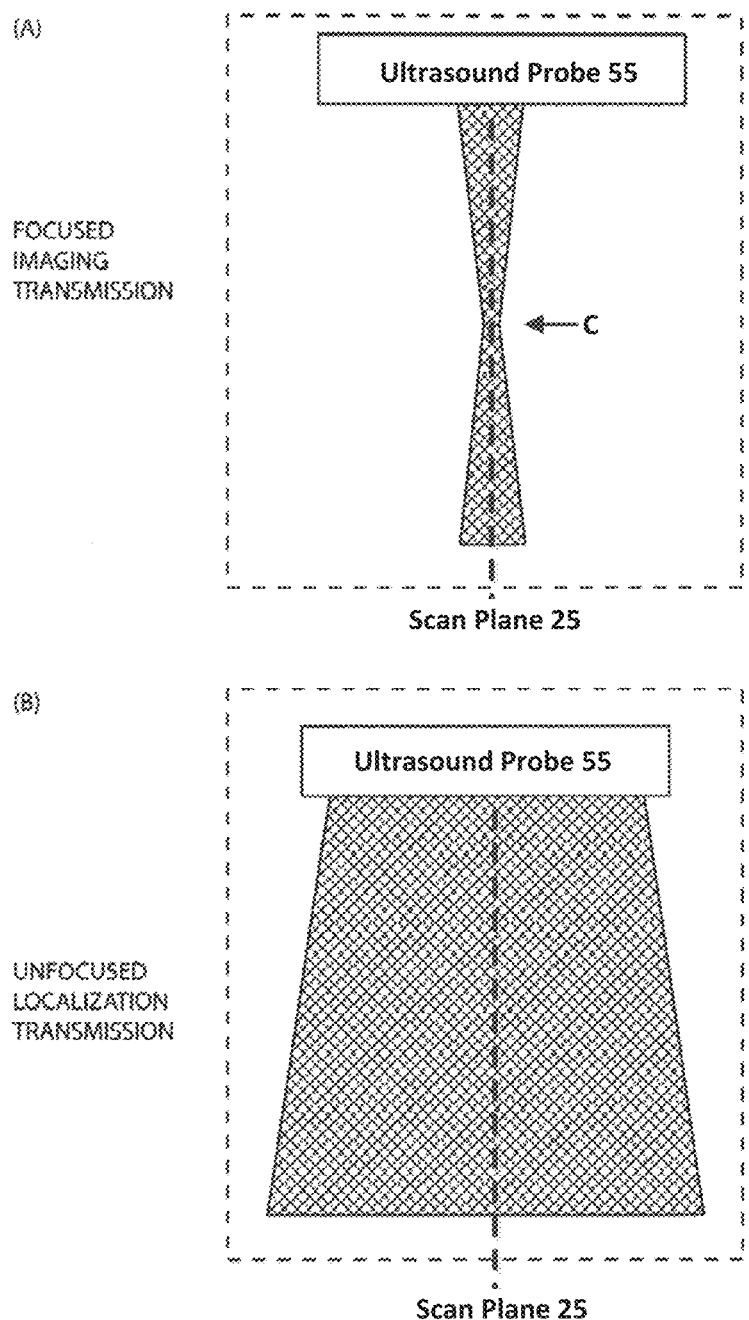
FIG. 5 is a schematic illustration of the imaging transmissions (A) and the localisation transmissions (B) produced by the ultrasound probe of FIG. 2 in accordance with one embodiment of the invention.

FIG. 5 provides a schematic illustration of ultrasound transmissions which are: (a) (top portion) focussed (imaging), and (b) (lower portion) unfocussed (localisation). These transmissions are represented by the hatched areas, and are depicted in the Y-Z plane (based on the orientation shown in FIG. 1). It will be appreciated that the "imaging transmissions" generally correspond to the transmissions produced by a conventional ultrasound probe, which are directed (focussed) into the imaging (scan) plane 25 in order to produce a reflected signal for obtaining anatomical images (the scan plane is shown schematically in FIG. 5 by a dashed line).

It will be appreciated that the imaging transmissions generally extend a small amount in the direction perpendicular to the scan plane 25. In practice, this means that the imaging scan plane is finite in width (rather than being infinitely narrow). Conventional ultrasound imaging systems do not discriminate position in this direction, but rather within the X-Y plane only. As shown in FIG. 5, the width of the imaging scan plane may vary a little with depth. In particular, FIG. 5 illustrates a point of convergence C, at which the imaging scan plane is most narrow. This point of convergence C provides the maximum axial and lateral pressure and corresponds to the depth in the patient body at which the ultrasound imaging system provides the best resolution. Some ultrasound imaging systems allow an operator to control the depth of this point of convergence (by altering the focussing of the imaging transmissions), so that the best resolution is obtained at a depth corresponding to the greatest anatomical or medical interest.

Referring now to FIG. 5, lower portion, the localisation transmissions are seen to extend over a much wider area than the imaging transmissions of FIG. 5, upper portion. In particular, the localisation transmissions extend significantly in the Z direction (perpendicular to the imaging plane 25) in comparison with the imaging transmissions. As described below, this extension of the localisation transmissions allows the tip of needle 70 to be detected, even when the tip of the needle is not located within the imaging scan plane 25.

Figure 6:
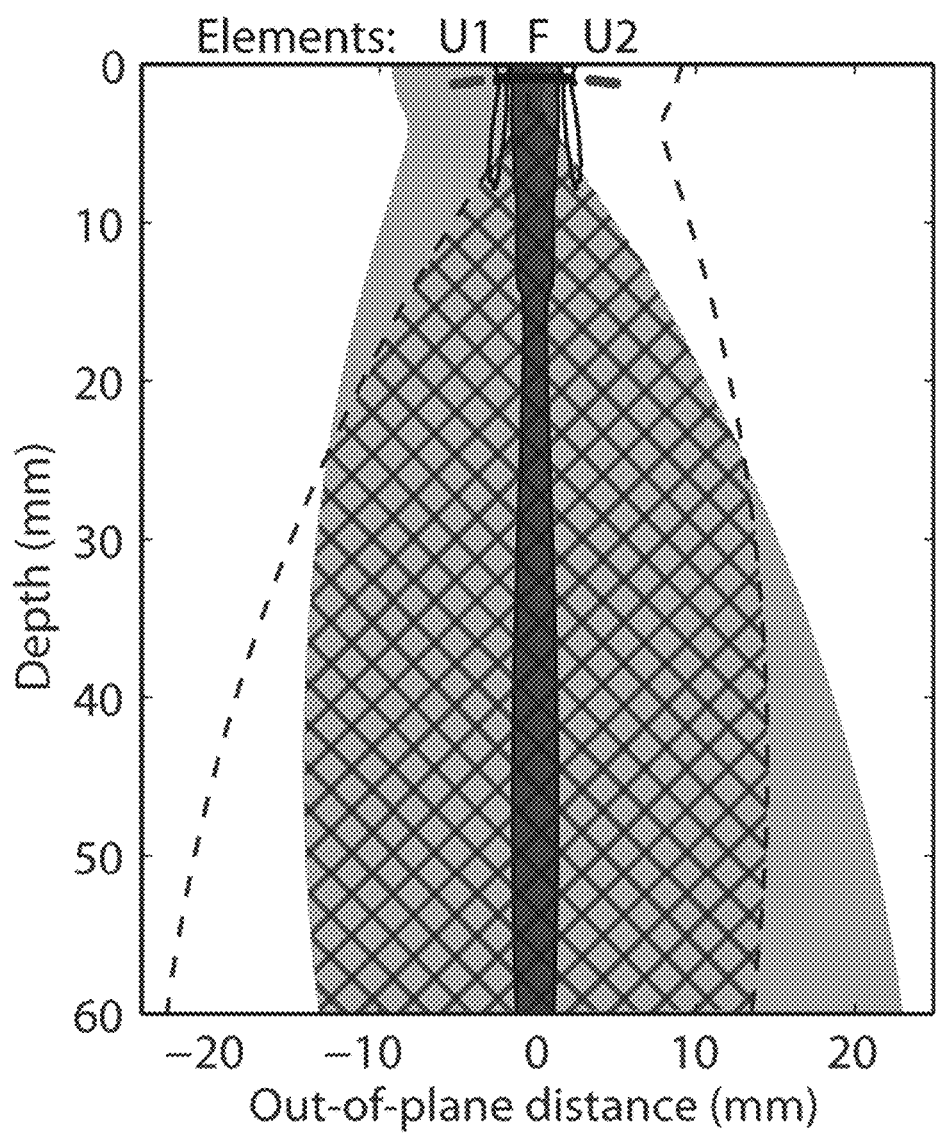
FIG. 6 illustrates in more detail the imaging transmissions and the localisation transmissions produced by the ultrasound probe of FIG. 2 in accordance with one embodiment of the invention.

FIG. 6 is another schematic illustration of the imaging and localisation transmissions from the ultrasound probe (using the same geometry as FIG. 5). As indicated at the top of FIG. 6, the ultrasound probe 55 includes two types of transducer elements. The first (conventional) set of transducer elements are denoted F and produce the imaging transmissions shown as the central dark stripe in FIG. 6. It will be appreciated that F may represent a line of separate transducing elements arranged along the top of the imaging scan plane 25, i.e. coincident with the line S-S in FIG. 1, which is perpendicular to the plane illustrated in FIG. 6. The second set of transducer elements, denoted U1 and U2, produce the localisation transmissions. Note that U1 and U2 are located on opposite sides of the imaging transducer elements F, and hence are separated in the Z direction, i.e. perpendicular to the image scan plane 25. (As with the imaging transducer elements F, U1 and U2 may each represent multiple localisation transducer elements, extending in a line parallel to the line S-S in FIG. 1).

The lightly shaded region of FIG. 6 represents localisation transmissions from transducing element(s) U1, while the dashed line represents the envelope of localisation transmissions from transducing element(s) U2. The hatched region of FIG. 6 then represents the overlap between the localisation transmissions from transducing element(s) U1 and the localisation transmissions from transducing element(s) U2. This hatched region generally represents the area in which the instrument transducer 123 located in a needle tip may be accurately located in three dimensions using the localisation transmissions. If the instrument tip is not in the hatched region, information about its position (e.g. the side of the imaging plane in which it resides) may still be obtained.

The localisation and the imaging is performed simultaneously or at least nearly (quasi) simultaneously in order to provide real-time feedback on the location of the medical instrument within the patient body. FIG. 6 illustrates the imaging transmissions and the localisation transmissions occurring at the same time, i.e. simultaneously. In some embodiments, if the imaging transmissions and the localisation transmissions occur at exactly the same time, there may be some interference between the two. For example, there may be the potential for reflections from the localisation transmissions to be detected by the ultrasound probe 55, thereby raising the effective noise level of the images produced by the ultrasound probe. One way of avoiding this is to use different frequencies for the imaging transmissions and the localisation transmissions, thereby allowing the ultrasound probe to discriminate between the two (and between reflections thereof). Another possibility is to intersperse the imaging transmissions and the localisation transmissions in quick succession in order to prevent interference between the two, but while still providing a physician with real-time feedback as to the position of the instrument relative to the scan plane.

In some embodiments, the imaging transmissions have a frequency above 4 MHz, for example in the approximate range 5-15 MHz, while the localisation transmissions have a frequency below 4 MHz, for example, in the approximate range 1-2 MHz. In general, the localisation transmissions are at a lower frequency than the imaging transmissions. This lower frequency helps the localisation transmissions to penetrate further into the patient body, and also reflects the lower degree of focussing which is required. The refresh rate for the localisation and imaging transmissions is generally at least 5 Hz, and usually higher, for example, in the range 20-60 Hz, to provide real-time feedback to a physician or other operation (the localisation and imaging transmissions may not necessarily have the same refresh rate). Note that even for a 50 Hz refresh rate, this still allows 20 ms per image or frame. In contrast, the return travel time for reflected imaging transmissions, which determines how long it takes to acquire an individual image, is usually much shorter (based on the size of a human body and ultrasound propagation speeds within the human body). Accordingly, localisation transmissions and the imaging transmissions can be interspersed if so desired without impacting the ultrasound frame rate.

The transducer elements U1, U2 producing the localisation transmissions are controlled so that the temporal pattern of the received ultrasound signal varies with location. Accordingly, as the acoustic transducer 123 receives the localisation transmissions and forwards them to console 65, the console (or some other processing device) is able to analyse the timings of the received signals to determine the location of the transducer 123 on the basis of these timings. There are various ways in which this may be achieved. In some embodiments, the transducer elements of the ultrasound probe 55 are operated in substantially the same manner, but with different timings (phase) in order to steer (electronically and/or mechanically) a wavefront in a desired direction. In other embodiments, individual transducer elements (or groups of transducer elements that are close together and function in effect as a single unit) transmit a signal having a unique identifier for that particular transducer element, so that the instrument transducer 123 can discriminate between the signals from the different transducers. In other embodiments, the localisation transducer elements transmit the same or similar signals, but the transducer elements are operated in turn, so that at any given time it is known which transducer element is currently transmitting.

Figure 7:
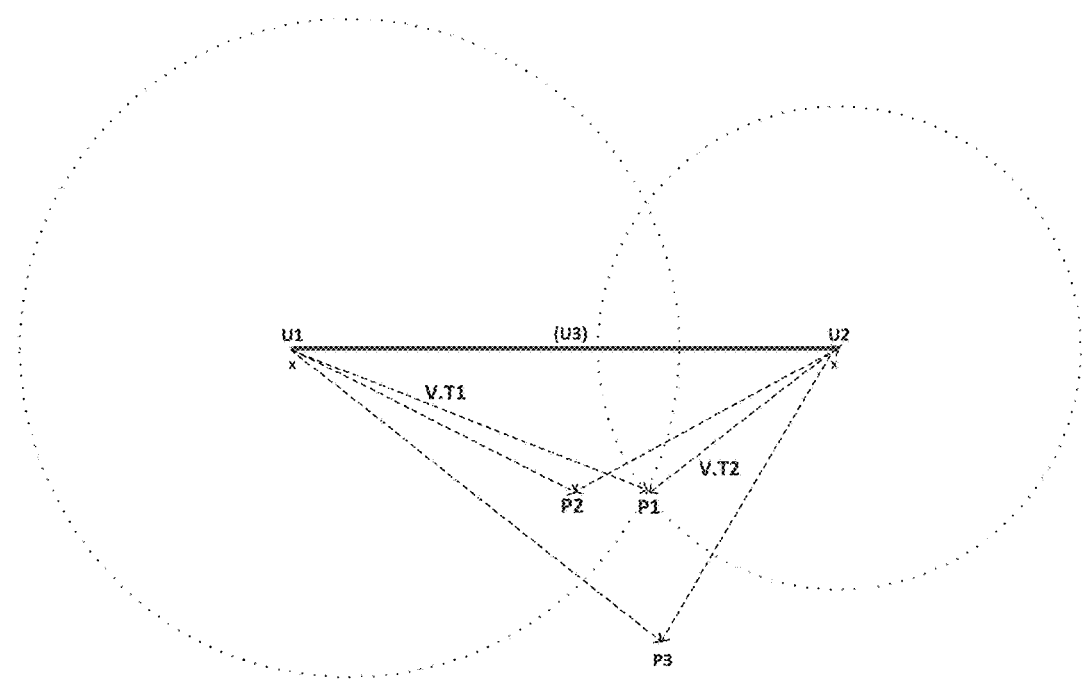
FIG. 7 is a schematic diagram of using the localisation transmissions to determine position based on time of arrival at the medical instrument in accordance with one embodiment of the invention.

FIG. 7 illustrates one possible mechanism for determining position using the approach described herein. We assume a substantially constant (and known) propagation speed V for the ultrasound signal within the human body, and that T1 and T2 represent the signal travel time to the instrument transducer 123 from the localisation transducing elements U1 and U2 respectively. If we consider just the Y-Z plane, we can then draw a circle around U1 of radius T1×V, and a circle around U2 of radius T2×V; the point of intersection (P1) of these two circles that resides in the patient then gives the location of the transducing element 123. Such a determination might be made by the processor 201 of the console 65 to allow the location of the transducing element 123 to be displayed on screen 68. Note that the speed of sound (V) of acoustic pulses in the human body, at the temperature of the human body, is generally known to the skilled person, and is utilised in many existing ultrasound imaging systems.

Two other locations are also shown in FIG. 7. Point P2 can be distinguished from point P1 by having reduced T1 and increased T2, in other words, the relative magnitude of T1 and T2 effectively determines motion parallel to the Z axis (perpendicular to the image scan plane 25). Point P3 can be distinguished from point P1 by having both T1 and T2 increased, in other words, the combined magnitude of T1 and T2 effectively determines motion parallel to the Y axis of FIGS. 5 and 6.

Although FIG. 7 illustrates localisation transducing elements of the ultrasound probe 55 at two different locations on the Z-axis, i.e. with a mutual spacing parallel to the Z-axis, in some embodiments there may be one or more further localisation transducing elements located at different (additional) spacings along the Z-axis, for example, at the location U3 indicated in FIG. 7. If transducing elements are provided at further spacings along the Z-axis, then the instrument transducer location is given by multiple separate intersections, which may or may not be exactly coincident with one another. The multiple different intersections can therefore be combined, e.g. by averaging or some other statistical technique, to given an overall best fit estimate for the location of the instrument transducer. Furthermore, the scatter between the different intersections can be used to derive the likely error associated with the estimated location of the instrument transducer.

Having more than two locations on the Z-axis can also assist with obtaining a location estimate without the need for exact synchronisation between the ultrasound probe 55 and the instrument transducer 123. For example, assume that the ultrasound probe 55 emits a signal at T(E) and the instrument transducer 123 detects a signal at T(D), then the signal travel time is T(D)−T(E)+ΔC, where ΔC is an (unknown) fixed offset caused by differences in clock settings, fixed delays in the system electronics, etc. In this case, we can then use the relative timings, i.e. T2−T1 and T3−T2 (with T1, T2 and T3 defined as above) to determine instrument location, with the unknown timing offset ΔC being effectively eliminated.

Although the discussion of FIG. 7 has concentrated on the Y-Z plane, as mentioned above, the localisation transducing elements of the ultrasound probe generally extend in direction of the X axis (as for the main imaging transducing elements). The timings from these transducing elements can then be used to locate the instrument transducer 123 in the X direction, as well as the Y-Z location illustrated in FIG. 7—i.e. a complete three-dimensional location can be obtained. One option is to focus the localisation transmissions in the X axis, and then to scan the localisation transmissions along the X axis (in a similar manner to how the imaging transmissions are scanned across the image scan plane 25).

In one implementation, the localisation timings are determined by transmitting a first pulse from one ultrasound localisation element (U1), detecting the first pulse at the instrument transducer 123, transmitting a second pulse from another ultrasound localisation element (U2) and then detecting the second pulse at the instrument transducer 123. As noted above, the travel times of the pulses from the ultrasound probe 55 to the transducer are very short (milliseconds or less), so that the instrument transducer can be assumed to have a constant location for both pulses.

Figure 8:
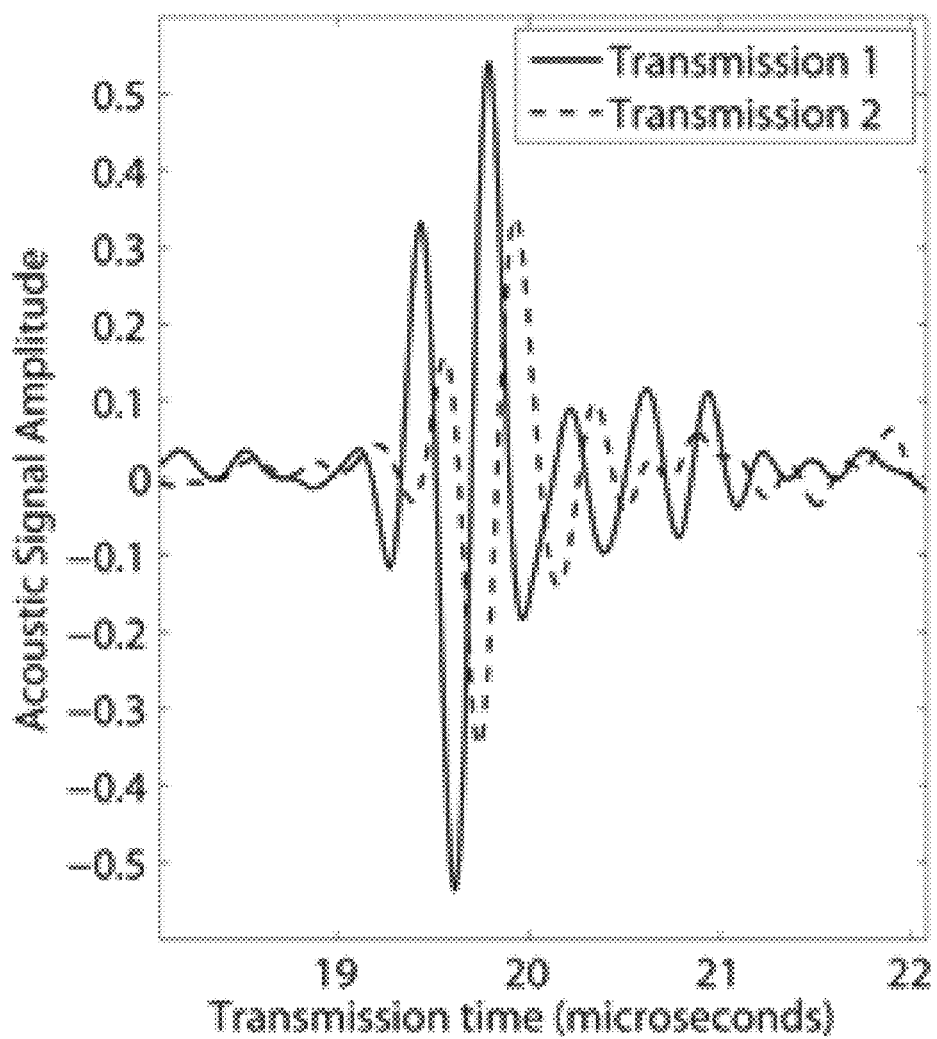
FIG. 8 illustrates experimental data showing ultrasound signals representing two different localisation transmissions as received at the medical instrument in accordance with one embodiment of the invention.

FIG. 8 illustrates the two signals received at the instrument transducer 123 when the instrument transducer is slightly closer to U1 than to U2. In particular, FIG. 8 plots experimental data for received signal amplitude against time from the pulse transmission (for each respective pulse), where the solid line represents the signal from U1, and the dashed line is the signal from U2. It can be seen that the transmission from U2 takes longer to arrive at the instrument transducer than the transmission from U1. This indicates that the instrument transducer is closer to U1 than U2, since the pulse travel time from U1 to the instrument transducer is shorter than the pulse travel time from U2 to the instrument transducer. In addition, the signal strength of the pulse from U1 is greater than the signal strength of the pulse from U2, which also implies that U1 is closer to the instrument transducer than U2, since the signal from U2 will therefore have suffered greater dispersion and attenuation. However, received amplitude tends to be a less reliable indicator of distance than transmission timing because the signal amplitude is more dependent on the nature of the transmission path.

Note also that the received signals in FIG. 8 are somewhat different in shape from a single pulse. This is primarily due to the (impulse) response of a transducer element when a transmission pulse is applied—in other words, if a single pulse is input to a transducer element, the signal that is coupled into the patient body tends to be more complex, such as shown in FIG. 8. Further distortion of the original pulse may occur during transmission through the patient body, especially if the ultrasound propagation speed is frequency-dependent (so that the different frequencies in the original pulse have slightly different propagation times to the instrument transducer).

If the impulse response of the ultrasound probe 55 and patient body 15 are estimated, an inverse filter function can be applied in the instrument transducer 123, transceiver 205, or processor 201. This filter can then reshape the signals of FIG. 8 approximately into a single pulse, thereby allowing a clearer measurement of the arrival time.

In the above embodiment, the pulses from transducers U1 and U2 are staggered, to allow a clear separation of the received signals at the instrument transducer. In other embodiments, the signals from the different transducers on the ultrasound probe may overlap. Nevertheless, the signals can be adapted to allow the signal from each instrument transducer to be individually identified.

Figure 9:
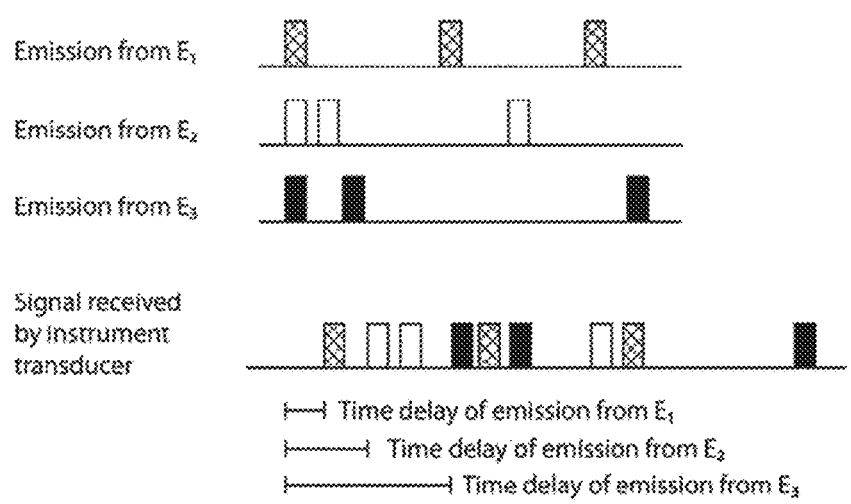
FIG. 9 is a schematic illustration of ultrasound signals from different localisation transducer elements, where each localisation transducer element transmits a different pulse sequence that can be separately identified in the overall ultrasound signal as received at the medical instrument in accordance with one embodiment of the invention.

FIG. 9 illustrates one way of providing each transducer element with its own distinctive (individual) signal Thus there are three transducer elements E1, E2, E3, each of which produces a pulse train having unique time separations, as shown in FIG. 9. The three transducer elements start to emit their respective pulse trains simultaneously, as shown in the top three lines of FIG. 9, while the lowest line in FIG. 9 represents the sequence of pulses received by the instrument transducer 123. From this received pulse sequence, the individual travel times from each transducer element can be determined ($T_1$, $T_2$ and $T_3$), therefore allowing a position estimate to be obtained, analogous to the approach shown in FIG. 7. As another example of each transducer element generating a unique (individual) transmission, the three imaging transducer elements E1, E2 and E3 may simultaneously emit a short burst of ultrasound. Each burst is allocated a different frequency band within the overall bandwidth (B) of the ultrasound probe 55. For example, if the imaging transducer has an operating frequency from F1 up to F2, where F=F2−F1, then E1, E2 and E3 can be assigned bursts within the frequency bands F1 to F1+(F/3), F1+(F/3) to F2−(F/3), and F2−(F/3) to F2. In processor 201 (or some other portion of the receiving system), the signals from the different transducer elements are separated using band-pass filters centered on the respective frequency ranges for the different transducer elements, and hence the timing of the individual acoustic emissions for E1, E2 and E3 can be recovered. Note that encoding emissions from different array elements using a frequency division approach is disclosed by F. Gran, et al., Proceedings of the IEEE Ultrasonic Symposium, pp. 1942-1946 (2003), but this is in the context of synthetic aperture imaging, which is significantly different from instrument localisation.

Another possibility is to use a code division multiple access (CDMA) scheme, in which different sets of localisation elements are assigned different sequences. CDMA schemes generally use sequences in the form of pseudorandom noise (PRN) codes, which are chosen to have low mutual cross-correlations and good auto-correlation properties (ideally zero for any non-zero offset). Well-known examples of PRN sequences used for CDMA schemes are Golay codes, Gold codes and Kasami codes.

In a CDMA scheme, signals are transmitted simultaneously from the different transducer elements, and are then separated (discriminated) using the code allocated to each transmitting element. For example, the processor 201 performs a cross-correlation of the (overall) received signal with all the codes for the different localisation transducer elements for all possible timing offsets (delays). When the correct timing delay for a given transducer element is used, this results in an auto-correlation peak that reveals the presence (and timing) of the signal from that transducer element. The timing delays for the different localization transducers are then used to determine the estimated location of the instrument transducer by the process illustrated in FIG. 7.

In embodiments where different transducer elements are assigned different identifying codes, the transducer elements may transmit the codes directly using a transmission scheme such as pulse code modulation (PCM). Alternatively, the codes may be used to perform phase or frequency modulation of an ultrasound carrier wave, such as by phase-shift keying (PSK) or some form of frequency modulation. The skilled person will be aware of various other mechanisms by which the transducer elements can transmit the codes, either directly or via some modulation scheme.

Having the localisation transducers emit different, identifiable signals allows signals to be transmitted simultaneously, which can reduce the overall time required for localisation. In addition, some form of patterning or coding, such as a distinct pulse code sequence, also helps to improve the signal-to-noise ratio of the received signal, because the receiver can look specifically for the distinct pulse code sequence, and this helps to filter out noise. Accordingly, a distinct pulse code sequence with a particular time structure (rather than just an individual pulse), might be used even if the localisation transducers are operated separately (without signal overlap). However, in this case, each localisation transducer could emit the same distinct pulse code sequence, rather than having to allocate a different sequence to each different localisation transducer element.

In embodiments which generate pulses from the localisation transducer elements, pulse compression techniques may be used to enhance the localisation accuracy. In such techniques, a pulse comprises a short time interval of sinusoidal waves (i.e. the pulse duration is at least several times greater than the period of the waves). Rather than having a constant frequency for the sinusoidal waves within the pulse, the frequency of these waves may be increased during the timing of the pulse. This is sometimes referred to as a chirp, because the frequency rises during the pulse. One benefit of this approach is that a suitably matched filter at a receiver, for example on or linked to the instrument transducer 123, can determine the timing of the pulse with greater accuracy than the timing of pulse at constant frequency. It will be appreciated that this increase in timing accuracy then translates into an increased signal-to-noise ratio with which to calculate the pulse travel distance, and hence a more accurate location for the instrument transducer. Different localisation transducer elements may transmit using different pulse compressions, and/or a single transducer element may use different pulse compression codes at different times (potentially depending on the most recently determined position of the instrument transducer).

Another location estimation technique may be utilise the phase of an incoming signal (as opposed to the absolute arrival time). Thus if a signal of speed V and frequency f is measured to have phase $\Phi$ (with respect to the signal as originally transmitted) then it follows that the travel time T is given by $T=(1/f) \cdot (n+(\Phi/2\pi))$, where n is an arbitrary integer (n=0, 1, 2, 3 . . . ). As a result, rather than having a single circle of possible locations from a given transducer element, such as shown in FIG. 7, the phase measurement defines a set of concentric circles about a given transducer element, each separated from the next by a distance of one wavelength (V/f). Since the signal from each transducer element produces its own set of concentric circles, then this leads to multiple points of intersection, and hence positional ambiguity.

If the phase is taken with respect to the acoustic frequency of an ultrasound signal (tone), then the wavelength is very short (1 mm or less for an ultrasound frequency of 1 Mhz or more), leading to a high level of positional ambiguity. On the other hand, very slight changes in the position of the transducer (of less than a millimeter) can be found based on a detected shift in phase. This can be useful if it is important to monitor very small (sub-wavelength) changes in the needle tip position which can be useful to determine the orientation of the distal end of the medical instrument since this distal end will move predominantly along its long axis. Alternatively (or additionally), a longer wavelength can be produced by modulating the raw ultrasound signal at the desired frequency. This reduces both the positional ambiguity and also the positional sensitivity—the spacing of the concentric circles is effectively increased, reducing the number of intersections, while a given shift in the detected phase now corresponds to a larger change in location. In some cases the positional ambiguity may be overcome by additional information, such as by utilising previous positional estimates, knowledge of the direction of insertion of the needle, visibility of at least part of the needle in the image scan plane, etc.

Another approach is to provide the localisation transmissions as a series of acoustic wavefronts, where each wavefront propagates in a substantially collimated fashion (diffraction at the edges of the wavefront is usually present). Such localization transmissions may be generated by the transmission of pulses from a plurality of acoustic elements, where the relative delays between pulses generated from adjacent elements of the imaging transducer determine the direction of propagation—analogous to a phased array. Wavefronts that propagate substantially in a collimated fashion such as "limited diffraction beams" are known (for example) from J. yu Lu, et al., IEEE Transactions on Ultrasonics, Ferroelectrics, and Frequency Control, vol. 53(10): 1796-1812 (2006). In such embodiments, the localisation transducers may be configured (for example) to produce a first wavefront that propagates in a substantially collimated fashion in a first direction, and is then followed closely in time by a second wavefront that propagates in a second direction which is offset from the first direction. Further wavefronts may be generated that likewise have an additional offset direction.

With this approach, each wavefront is produced by a coordinated set of transmissions from multiple localisation transducers, and the instrument transducer 123 is unable to discriminate a signal from any single transducer element. However, by altering the direction of successive wavefronts, the timing between the receipt of successive wavefronts varies according to location within the body. Therefore the location of the instrument transducer can be determined from the arrival times of successive wavefronts.

Figure 10:
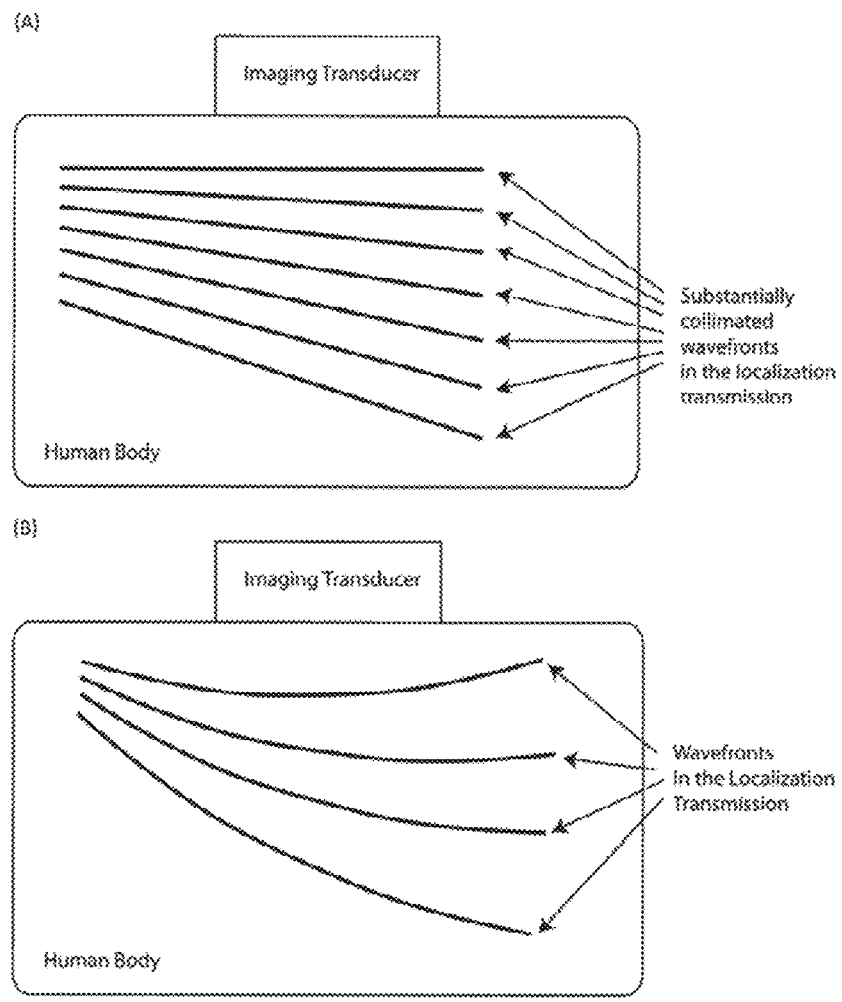
FIG. 10 is a schematic illustration of localisation transmissions comprising successive wavefronts that have been steered in different directions in accordance with one embodiment of the invention.

FIG. 10 provides two-dimensional representations (in the Y-Z plane) of two different forms of wavefront for the localisation transmissions. The direction and shape of each wavefront is controlled or steered based on phase differences applied across the localisation transducer elements. The linear wavefronts shown in FIG. 10, top portion (a) correspond to a linear increase in phase with position (along the Z-axis) of the localisation transducer, where the rate of increase is slowly raised between successive wavefronts to produce the change in direction. In contrast, the curved wavefronts shown in FIG. 10, bottom portion (b) correspond to a nonlinear change in phase with position of the localisation transducers.

Although FIG. 10 illustrates only the Y-Z plane, the direction in which each wavefront propagates can be varied in three dimensions depending on the configuration of the transducers on the ultrasound probe. In particular, the direction along the X-axis can be controlled (varied) provided the ultrasound probe 55 includes localisation transducer elements spaced along the X-axis—i.e. an overall 2D array of such elements in the X-Z plane). Note also that the ultrasound probe 55 may generate simultaneously two (or more) sets of wavefronts propagating in different directions, for example, the wavefronts for different directions could be generated using different portions of the transducer bandwidth (i.e. using different frequencies).

The minimum delay between the successive wavefronts is generally significantly less than the period between consecutive imaging transmissions. In particular, the latter period is usually set sufficiently long so that signals generated by acoustic pulses reflected from deep structures are not confounded with acoustic pulses reflected from superficial structures in a subsequent imaging transmission. However, this constraint is typically not relevant for the localisation transmissions, and therefore the wavefronts can be spaced more closely in time (compared with imaging transmissions).

Figure 11A:
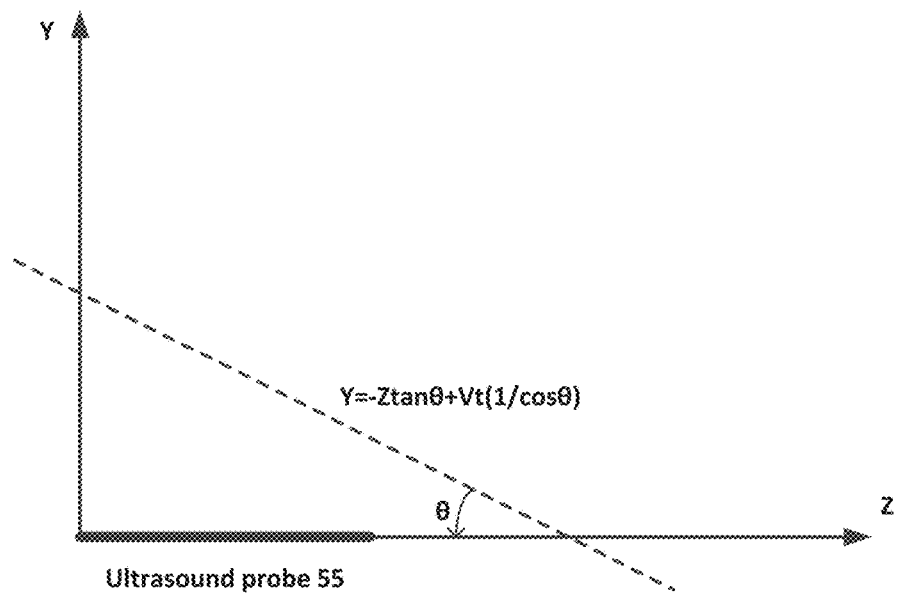
FIGS. 11A and 11B illustrate in schematic form the use of the localisation transmissions shown in FIG. 10 to determine position of the medical instrument in accordance with one embodiment of the invention.
Figure 11B:
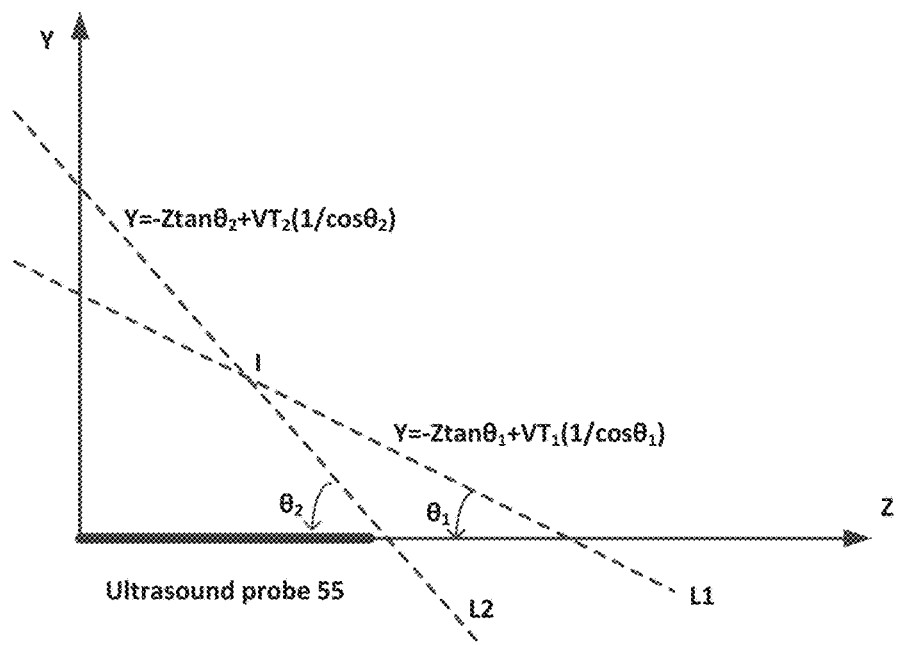

FIGS. 11A and 11B illustrate the principle of locating the instrument transducer using successive wavefronts having different directionality. In both Figures, the localisation transducer elements of the ultrasound probe 55 are assumed to lie along the z-axis as shown, while the y-axis represents the direction into the patient body (shown upwards for convenience, rather than downwards as in FIG. 1). The transducer elements generate one or more wavefronts that propagate into the body at an angle $\theta$ to the Z-axis. Assuming a constant speed V for the propagation of the wavefront through the body, the location of the wavefront at a time t is given by the equation $Y=-Z \cdot \tan \theta + (V \cdot t / \cos \theta)$, as shown in FIG. 11A, where t is set to zero when the wavefront passes through the origin. Note that the angle $\theta$ is assumed to be known based on the relative timing delay between the transducer elements within probe 55.

FIG. 11B shows the situation where two wavefronts have been received at the instrument transducer 123, the first wavefront L1 at a time $T_1$ and with a (known) angle of propagation of $\theta_1$, the second wavefront L2 at a time $T_2$ and with a (known) angle of propagation of $\theta_2$. Assuming that V is again constant for both wavefronts, we can plot the location of the two wavefronts at the time of their respective reception by the instrument transducer. It will be appreciated that the intersection (I) of these two lines L1, L2, corresponds to the location of the instrument transducer 123.

Although FIGS. 11A and 11B illustrate a two-dimensional localisation, a three-dimensional localisation could be performed by detecting the arrival time $T_3$ of a third wavefront propagating in a different direction to the first and second wavefronts. In particular, the propagation direction of the third wavefront should lie out of the z-y plane in order to provide location along the x-axis (not shown in FIGS. 11A and 11B). Given the three time differences, ($T_1$, $T_2$, and $T_3$), with each time difference corresponding to a wavefront with its own direction of propagation, there is generally a unique relationship between the time differences and the position of the instrument transducer in three-dimensional space (x,y,z) (analogous to the two-dimensional example shown in FIGS. 11A and 11B). This relationship then allows an estimate of the instrument transducer position to be calculated. In particular, the value of $T_1$ constrains the estimated position of the instrument transducer to a first two-dimensional surface that corresponds to the first wavefront after propagation by a time $T_1$; the value of $T_2$ constrains the estimated position of the instrument transducer to a second two-dimensional surface corresponding to the second wavefront after propagation by a time $T_2$; and the value of $T_3$ constrains the estimated position of the instrument transducer to a third two-dimensional surface corresponding to the third wavefront after propagation by a time $T_3$. Note that although FIGS. 11A and 11B depict flat wavefront surfaces, the same approach can be utilised with curved wavefronts (such as shown in FIG. 10, lower portion (b), providing the location of the wavefront at any given propagation time can be determined (or estimated).

Accordingly, the processor 201 analyses the signals received from the instrument transducer 123 to detect the wavefront for each localization transmission as it arrives at the instrument transducer; the time difference between the arrival of each individual wavefront and the start of the transmission is calculated; and the set of time differences for the various wavefronts is processed to derive an estimate of the position of the instrument transducer 123. It will be appreciated that a number of pre-processing procedures may be performed on the incoming signal to facilitate detecting the incidence of an acoustic wavefront at the instrument transducer, such as bandpass filtering with a filter matched to the bandwidth of the localisation transducers.

Analogous to detecting a signal from more than three localisation transducers (as discussed above), if more than three wavefronts having different directionality are received, then correspondingly more than three arrival times can be calculated. The additional wavefronts allow a more accurate position estimate to be obtained for the instrument transducer, plus an indication of error, either by averaging different estimates from different sets of three wavefronts, or by utilising all the arrival time information together to calculate one overall estimated position. Conceptually, these additional wavefronts represent extra lines in FIG. 11B that should all pass through point I, the location of the intersection of L1 and L2. In practice, the intersections will not be exactly coincident with one another because of noise, slight variations in propagation speed, etc. However, if the intersections are all within a small area, this gives a high confidence (low uncertainty) for the positional estimate; conversely, if the intersections are spread out across a large area, this gives a lower confidence (higher uncertainty) for the positional estimate.

The calculation of the position estimate for the instrument transducer can also take into consideration uncertainties in the individual timing measurements (irrespective of whether they are performed on a signal from one or from more than transducer element). Thus if the instrument transducer obtains a clear signal peak corresponding to the arrival of a wavefront or pulse, then this arrival time can be determined relatively accurately. However, if the signal peak corresponding to the arrival of a wavefront or pulse is more blurred, for example because of noise and/or effects discussed in relation to FIG. 8, the arrival time might be determined less accurately. An appropriate measure of the uncertainty in the determined arrival times can be carried through into the position estimate of the instrument transducer—e.g. the estimate calculation may place more reliance on (i.e. increase the relative weighting of) those timing measurements which are known to have greater accuracy.

The estimated position based on a given set of timing measurements can be determined by solving a set of equations, such as shown in FIG. 11A (extended to three-dimensions), one for each wavefront/pulse/code, via some suitable analytical or numerical technique. Another option is to use a look-up table which maps the time differences to an estimate of the instrument transducer position. The lookup table (or parameters used for an analytical or numerical solution) may be generated theoretically or experimentally. As an example of the latter approach, a look-up table might be generated by varying the position of an instrument transducer in a tissue phantom (for example a water bath) and obtaining a set of time differences for each position. To estimate the position of an instrument transducer in the human body, the time differences in the look-up table that are closest to those obtained from the human body are identified, and the corresponding instrument transducer position in the look-up table can then be given as the estimate of the instrument transducer position in the human body.

In one embodiment, the ultrasound image display 68 is configured as shown in FIG. 2 to display both a conventional ultrasound anatomical image of the human body from the ultrasound probe 55, as generated by the imaging transmissions, plus an indication of the estimated position of the instrument transducer 123 determined from the localisation transmissions. (As discussed above, the imaging transmissions and the localisations transmissions may be interspersed, to provide quasi-simultaneous imaging and localisation). The position indication for the instrument transducer can be provided by any suitable mechanism, for example, using an arrow, a circle, or any other shape superimposed on the anatomical ultrasound image, where the location of the shape reflects the estimated position of the instrument transducer. One option is to colour the shape differently depending on whether the estimated position for the instrument transducer lies within or outside the scan plane. An en-face cross-section can also be provided to show the position of the instrument transducer relative to the scan plane, such as shown in FIG. 2.

In some implementations, there may be a direct (known) geometric relationship between the position of the instrument transducer and a second position for the instrument, for example, that of a needle tip. In this case, the second position might be displayed in addition to, or in place of, the position of the instrument transducer. For example, if the instrument is a needle and the angle at which it is inserted into tissue is known by means of the estimated trajectory (e.g., spatial position as a function of time of the instrument transducer through the human body), and if the distal end of the instrument is known to be located a particular distance along the long axis of the needle from the transducer, then the position of the distal end of the needle can be readily determined from the estimated transducer position. The distal end of the needle can then be displayed on the anatomical image in addition to, or in place of, the position of the instrument transducer.

Another possibility is that based on an estimate of the instrument transducer position obtained from the localisation transmissions, the direction in which the instrument transducer should be moved by the practitioner in order to locate the instrument transducer inside the scan plane is calculated and indicated on the anatomical image display. Further, if the uncertainty of the estimated position for the instrument transducer position is calculated, such an uncertainty can be indicated on the display, for example, by displaying a circle with a diameter that is related to the size of the error. Another option is to use the transparency, colour or size of the shape indicating the estimate position of the instrument transducer to reflect the uncertainty associated with this estimate. In some cases, a specific warning may be provided if the error is above (or suspected to be above) a user-specified value, for example, the shape indicating the position of the instrument transducer might be made to blink, or be supplemented by a warning symbol (e.g. visual, audible, and/or tactile).

The localisation estimates described above, such as illustrated in FIGS. 7 11A, and 11B, are derived from a single set of measurements—i.e. timing measurements in respect of the present position of the transducer 123. However, the system will generally produce a time series of such measurements, which therefore allows the trajectory or motion of the transducer to be estimated. Accordingly, in some embodiments, the current position is estimated not only from the (new) timing measurements in respect of the present position of the transducer 123, but also by extrapolating (predicting) from previously estimated positions. There are various known mechanisms, such as Kalman filtering, which combine these two pieces of information, namely the new position measurement and the extrapolation from previous measurements, to produce a single, overall estimate for the new (current) position. The use of previous measurements in this manner to supplement the new position measurement generally provides a more reliable estimate of position, for example, it reduces the susceptibility to noise in respect of any single measurement.

Information concerning one or more previously determined locations for the instrument transducer 123 can also be used to control various properties of the localisation transmissions, such as intensity, timing, pulse code compression scheme, and so on. More generally, the properties of the localisation transmissions may be varied according to the known (e.g. previously measured) location and/or signal properties received by the instrument transducer. For example, if the needle transducer signal level is high, such as when the instrument transducer is relatively close to the surface of the human body (and hence relatively close to the ultrasound probe 55), then the localisation transmissions can be reduced in intensity, or changed to a format or type that provides lower acoustic energy. The choice and setting of the localisation transmissions may also depend on the estimated depth of the instrument transducer: for example, at large depths, the intensity of the localisation transmissions might be increased and/or the ultrasound frequency of the localisation transmissions reduced to ensure a reliable signal is still received at the instrument transducer. Another possibility at such larger depths is to bias the acoustic energy from the localisation transducers towards higher frequencies to compensate for greater attenuation at higher frequencies. Conversely, while at shallower depths, the acoustic energy may be distributed more equally among frequencies in the bandwidth of the localisation transducers. The signal strength of the localisation transmissions might also be increased (manually or automatically) if the instrument transducer gets close to a particularly sensitive anatomical feature—this increased signal strength can help to improve the accuracy of the localisation. Similarly, if the instrument transducer 123 is determined to be moving relatively rapidly, then the localisation transmissions and resulting position determinations might be repeated more frequently in order to maintain positional accuracy for the localisation. Additionally, the signal strength of the localisation transmissions may alternate automatically as a sequence, with said sequence not necessarily dependent on information concerning one or more previously determined locations for the instrument transducer 123). In that case, estimates for the locations of the instrument transducer may be obtained with only a subset of the localisation transmissions, with the choice of said subset dependent on certain calculated properties of the signals received by the instrument transducer (e.g. signal amplitude).

The instrument transducer position and any other quantity calculated and/or determined using the localisation transmissions may also be shown on a display which is distinct from the anatomical image display 68. For example, such a display might be included on the instrument 70 itself or on a mechanical component that is connected to the instrument, or provided in the form of a heads-up display on glasses, a 3D screen, or a holographic display. An auditory signal may also be provided, such as a tone that varies in frequency depending on the extent to which the instrument transducer is out of the scan plane 25. Furthermore, if a second image from a different imaging modality, such as MRI or CT, is co-registered with the ultrasound image, the instrument transducer position may also be indicated with respect to this second image.

Figure 12:
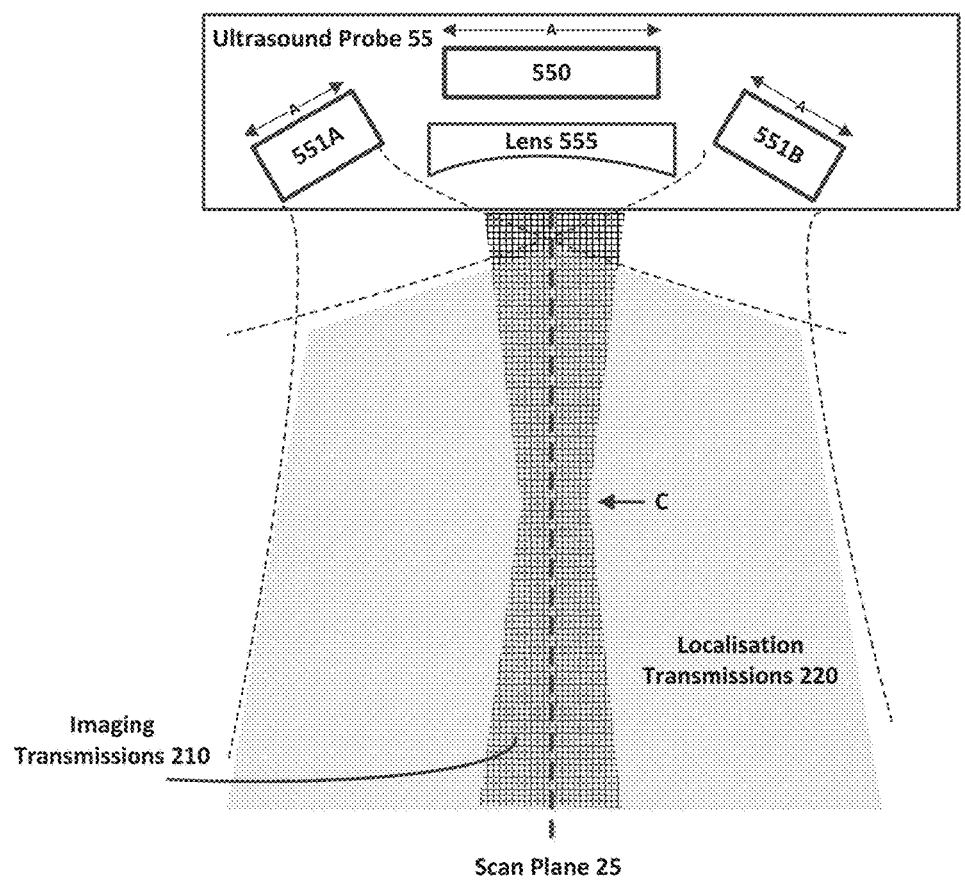
FIG. 12 is a schematic diagram showing the ultrasound probe of FIG. 2 together with the imaging and localisation transmissions in accordance with one embodiment of the invention.

FIG. 12 is a schematic diagram illustrating one embodiment of ultrasound probe 55. This is shown with the same geometry as FIG. 6, i.e. in the Y-Z plane, perpendicular to the lateral dimension of the ultrasound probe 55 (corresponding to direction S-S in FIG. 1). The ultrasound probe 55 includes one or more imaging transducers 550 for producing the imaging transmissions 210, as shown in FIG. 12 by the hatched area. The ultrasound probe 55 also includes a mechanism for focussing the imaging transmissions 210 within the scan plane 25. In the embodiment shown in FIG. 12, the focussing mechanism comprises an ultrasound lens 555. (Note that for ultrasound waves, lens 555 may have a concave shape to provide focussing, in comparison with a convex shape normally used for optical focussing). Different implementations may use different or additional focussing mechanisms, such as: curvature of the imaging transducer (s), one or more ultrasound reflectors, collimation, electronic steering (e.g. by relative timing), etc. The focussing of the imaging transmissions may also be achieved, at least in part, by having multiple imaging transducers 550 that are separated along the Z-axis—such a configuration is known, for example, to control the depth of point C, the location of maximum focus. Note that even though such multiple imaging transducers 550 may be separated along the Z-axis, their transmissions are still focussed into the scan plane 25.

The ultrasound probe 55 further includes at least two localisation transducer elements 551A, 551B, which are separated along the Z-axis, to produce the localisation transmissions 220. FIG. 12 shows as lightly shaded the region in which localisation transmissions are received from both localisation transducer elements 551A, 551B. This is the region in which a localisation position can generally be obtained, for example, by following the approach illustrated in FIG. 7.

In some embodiments, the localisation transmissions may, in effect, scan through the volume or region of particular interest (i.e. outside the lightly shaded region of FIG. 12), analogous to the way in which the imaging transmissions may scan through the scan plane 25. This scanning may be accomplished by various techniques, such as by one or more of the following: mechanical movement of the localisation transducer elements; mechanical movement of a lens or other focussing arrangement; mechanical movement of an ultrasound mirror or other reflective device; electronic steering. The scanning may be performed using a sequence of localisation transmissions that move through the volume or region of particular interest in a continuous or discrete manner.

As shown in FIG. 12, the localisation transducer elements 551A, 551B are different from the imaging transducer elements 550. In other words, the ultrasound probe 55 does not comprise a two-dimensional, homogeneous array of transducer elements that can be controlled at different times to generate imaging or localisation transmissions. Rather, the ultrasound probe 55 comprises a heterogeneous set of transducer elements: a first set comprising imaging transducer elements having a substantially linear arrangement along the line S-S (see FIG. 1), and a second set comprising localisation transducer elements that are spaced in a direction perpendicular to the scan plane (i.e. along the Z-axis). The imaging transducer elements and the localisation transducer elements are distinct and dedicated to their respective tasks (of producing imaging and localisation transmissions respectively). The design and operation of the imaging transducer elements and the localisation transducer elements is arranged to reflect (and support) these different tasks.

Thus in some embodiments, the localisation transducer elements have a different size and/or structure from the imaging transducer elements. For example, the localisation transducer elements may be smaller than the imaging transducer elements, since the former only need to produce an ultrasound signal which is strong enough to be detected by the instrument transducer 123, whereas only reflections of the imaging transmissions are detected (and such reflections may be very weak depending on particular structures within the body). Furthermore, the localisation transmissions may utilise a form of coding or modulation such as discussed above to improve the signal-to-noise ratio received at the instrument transducer 123, whereas such a strategy may not be used for imaging transmissions. Thus with reference to the dimension denoted "A" in FIG. 12, the localisation transducer elements may (in certain embodiments) have a size in the range 1-3 mm (say 1.75 mm), compared with a size of 2-6 mm (say 4 mm) for the imaging transducer elements.

In addition, the localisation transducer elements 551A, 551B will generally (although not necessarily) operate at a lower frequency compared with the imaging transducer elements 550, since a lower frequency ultrasound signal will penetrate further into the human body and will tend to be less collimated, while a higher frequency will give better imaging resolution (without necessarily impacting the travel time measurements used for localisation). For example, the localisation transducer elements 551A, 551B may operate at a frequency somewhere in the range 1-2 MHz (say 1 MHz), while the imaging transducer elements 550 may operate at a frequency somewhere in the range 5-15 MHz (say 15 MHz). Having different frequencies for the imaging and localisation transmissions also reduces the risk of interference if the two transmissions are made simultaneously (rather than one after the other in closely spaced intervals).

The localisation transducer elements 551A, 551B and the imaging transducer elements 550 will also generally differ from one another in view of the different spatial distributions of the localisation and imaging transmissions, including their different respective focussing requirements. For example, the imaging transducer elements are provided with a significant focussing capability, such as a lens 555, curvature, or any other appropriate focussing mechanism, to restrict the imaging transmissions substantially to the scan plane 25. In contrast, the localisation transducer elements are configured to produce localisation transmissions across a much more extensive volume, such as shown in FIG. 12. In general, the localisation transducer elements will therefore be provided with only weak (or no) focussing, and hence will have a different (or no) focussing mechanism (lens, curvature, etc.) compared to the imaging transducer elements. In some cases, the localisation transducer elements may be provided with at least one lens to spatially broaden (defocus) the localisation ultrasound transmissions (analogous to the effect that a concave lens has on collimated optical light). Different localisation transducer elements (or different groups of the localisation transducer elements) may be provided with different lens configurations (or no lens) in order to distribute the localisation ultrasound transmissions more broadly away from the image scan plane 25. Furthermore, the localisation transducer elements may have a (slightly) different orientation from the imaging transducer elements, such as shown in FIG. 12, in which the localisation transducer elements are tilted with respect to the imaging transducer elements so that the localisation transmissions cover the desired volume.

In some embodiments, the localisation transducer elements are able to direct (and/or focus) the localisation transmissions in a direction parallel to the Y-axis, i.e. in terms of depth into the body, but are unfocussed in a direction parallel to the Z-axis, i.e. perpendicular to the image scan plane 25. The depth of focus of the localisation transducer elements may be varied, analogous to the imaging transmissions, in effect to scan to different depths. The localisation transducer elements may be controlled so as to focus at a different depth from the focus of the imaging transducer elements. This can help the localisation transducer elements and the imaging transducer elements to operate at the same time (concurrently), but without the transmissions from the former interfering with the reflections of the latter (and hence adversely affecting the resulting ultrasound image). The localisation transducer elements may also be able to direct (and/or focus) the localisation transmissions away from the image scan plane 25, thereby helping to avoid interference between the localisation transmissions and the imaging transmissions.

In some embodiments, localisation transmissions from different localisation transducer elements (or groups of localisation transducer elements) may be electronically focussed to different spatial regions. In other words, first localisation transmissions from one group of localisation transmissions may be focussed to one region, while second localisation transmissions may be focussed to a second spatial region which is distinct and separate from the second spatial region. The localisation transmissions from the first group may be simultaneous with the localisation transmissions from the second group. Note that in this case, the localisation transmissions from different localisation transducer elements (or groups of localisation transducer elements) may be individually identifiable using previously mentioned techniques (e.g. a CDMA scheme). Similarly, if the localisation transmissions from one or more (groups of) localisation transducer elements are scanned across the region outside the image scan plane 25, then the timing of when the transducer receives the scanned signal indicates the lateral position of the transducer in the S-S direction (somewhat analogous to conventional scanning in the image plane).

Figure 13A:
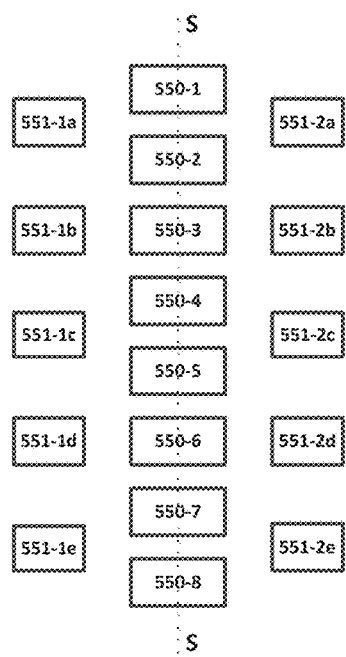
FIGS. 13A and 13B are schematic diagrams showing two examples of the configuration of imaging and localisation transducer elements within the ultrasound probe of FIG. 2 in accordance with one embodiment of the invention.
Figure 13B:
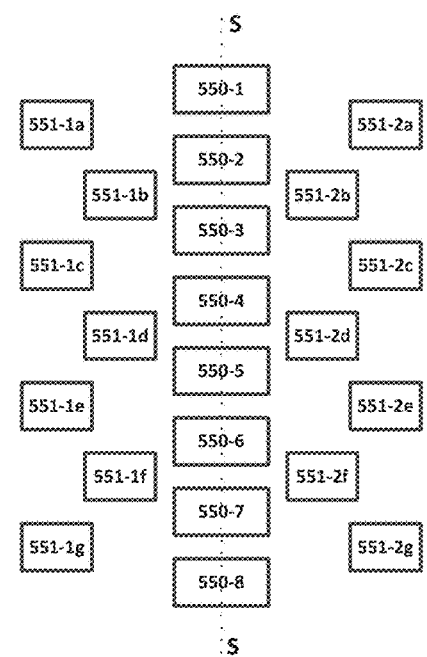

FIGS. 13A and 13B illustrate two different embodiments of the ultrasound probe 55 as shown in the X-Z plane, where the ultrasound probe 55 has a generally linear configuration about axis S-S as per FIG. 1. (Note that in practice the ultrasound probe 55 will generally have the pattern of transducers repeated more times in the S-S direction than shown in FIGS. 13A and 13B, thereby giving the overall configuration a more linear, less planar appearance). The main axis (S-S) of the ultrasound probe comprises a central line of imaging transducers 550-1, 550-2 and so on. This central line of imaging transducers is then flanked on each side by a line of localisation transducers, namely 551-1a, 551-1b, etc. and 551-2a, 551-2b, etc. This arrangement allows the central line of imaging transducers to be based on a conventional (1-D) ultrasound probe, thereby allowing the localisation transducers to be more readily accommodated in existing devices and procedures.

In the embodiment shown in FIG. 13A, the localisation transducers are arranged at two positions along the Z-axis (perpendicular to the line S-S and the scan plane), thereby giving a single spacing along the Z-axis—corresponding to the configuration shown in FIG. 7. In the embodiment shown in FIG. 13B, the localisation transducers are arranged at four different positions along the Z-axis, see e.g. 551-1a, 551-1b, 551-2a and 551-2b. As discussed above, this generally allows multiple position determinations in the Z direction, which can give more accurate results overall. In addition, since the configuration of transducers extends in the X-direction (parallel to the line S-S), as well as in the Z-direction, this allows the instrument transducer 123 to make a full three-dimensional determination of its (the instrument transducer's) position within the patient body 15.

It will be appreciated that the precise number, location and configuration of the imaging and localisation transducers will vary according to the particular design and requirements of any given implementation, having regard to the fact that the ability to locate the instrument transducer 123 in three-dimensional space generally involves a planar (rather than linear) array of localisation transducer elements. Nevertheless, the ultrasound probe may still be primarily linear overall, in other words, the transducer elements are configured so that the dimension along the X-axis (parallel to the line S-S in FIG. 1) is significantly greater than the dimension along the Z-axis (perpendicular to the image scan plane 25), although there may be more than one row of imaging elements. This configuration conforms to the majority of existing ultrasound devices, and hence is easier for a physician to operate.

In some implementations, the ultrasound probe may be provided with one or more mechanical scanning elements to generate a three-dimensional image by mechanically scanning a linear array of localisation transducer elements, thereby creating in effect a planar array of transducer elements. Instead of moving the localisation transducer elements themselves, the ultrasound probe may be provided with reflectors or similar devices, and these instead might be used to provide mechanical scanning and hence to create, in effect, a planar array of localisation transducer elements. In such an arrangement involving some form of scanning mechanism, the position of the instrument transducer relative to the ultrasound probe 55 can be estimated based on the localization transmissions received at the instrument transducer for different mechanical scan positions, in combination with information provided about the variation in mechanical scan position with time. In addition (or alternatively), the lens configuration provided to a given localisation transducer element (or to groups or all of the localisation transducer elements) may be varied dynamically. For example, different localisation transmissions could be generated at different points of time with different lens curvature and/or different lens properties (or by changing whether or not a lens is used for a given portion of the localisation transmissions).

Considering now the needle 70 shown in FIG. 3, it will be appreciated that many medical needles utilized in percutaneous interventions have a diameter of 22-gauge (e.g., outer/inner diameter: 0.7176 mm/0.413 mm) or smaller, and many have a length greater than 50 mm. Hydrophones (ultrasound sensors suitable for use in a substantially aqueous environment, such as a human body), may be constructed from polyvinylidene fluoride (PVDF), and are commercially available with diameters of 0.04 mm. Such a hydrophone could in principle be used for transducer 123. However, PVDF hydrophones currently tend to be expensive, fragile, and are often sensitive to electromagnetic interference. Fiber optic hydrophones, in which optical waves are detected with light delivered and received by a single optical fiber, are sufficiently small to fit within a 30-gauge hypodermic needle, and in most cases variations in the length of the optical fiber to accommodate different needle types have a negligible impact on their sensing properties. Many types of fiber optic hydrophones currently exist, with sensing mechanisms such as reflections in a Fabry-Perot cavity—see for example, U.S. Pat. No. 5,311,485, US 2004/0071383, U.S. Pat. Nos. 7,224,465, 6,813,401, J. J. Alcoz et al., IEEE Transactions on Ultrasonics, Ferroelectrics, and Frequency Control, 37(4), pp. 302-306 (1990), J. F. Dorighi et al., IEEE Transactions on Ultrasonics, Ferroelectrics, and Frequency Control, 42(5), pp. 820-824 (1995), P. C. Beard et al., Applied Optics, 35(4), pp. 663-675 (1996), P. C. Beard, Electronics Letters, 33(9), pp. 801-803 (1997), P. C. Beard et al., Proceedings of the IEEE Ultrasonics Symposium, pp. 1881-1883 (1998), P. Beard, et al., IEEE Transactions on Ultrasonics, Ferroelectrics, and Frequency Control, vol. 47(1): 256-264 (2000), Acquafresca, Proceedings of IEEE: Sensors, 2002, pp. 261-265 (2002), Acquafresca, IEEE Transactions on Ultrasonics, Ferroelectrics, and Frequency Control, 50(10), pp. 1325-1335 (2003), E. Biagi et al., Proceedings of the IEEE Ultrasonics Symposium, pp. 556-559 (2006) and E. Biagi et al., Journal of Sensors, Article ID 917314 (2010). U.S. Pat. No. 4,155,065 discloses a hydrophone with a sensing mechanism based on the optical scattering of light in a diffuse medium.

Although many hydrophones are available, the integration of such hydrophones with medical needles remains difficult, especially for needles that are thin and long. The bevel surface of a medical needle is typically angled to facilitate passage through tissue, i.e. the surface normal is not parallel to the longitudinal axis of the needle cannula. This geometry differs from that of the distal end of a typical fiber optic hydrophone. This can lead to the problem of how to maintain the angled bevel surface, while at the same time allowing acoustic waves to reach the sensing surface of the hydrophone. Another problem is how acoustic waves from the imaging transducer that impinge on the needle at a broad range of angles are to be efficiently directed towards the sensing surface of the hydrophone. For example, Acquafresca et al. (cited above) describes a probe that includes an optical fiber hydrophone with a Fabry-Perot sensing element that can be inserted into the cannula of a needle. However, since the probe has a non-angled bevel surface, it is not integrated into a needle stylet, and therefore it is not well-suited to use during insertions of the needle.

The integration of the transducer 123 (such as an optical hydrophone) into the medical needle 70 shown in FIG. 3 to receive ultrasound transmissions therefore has to address various problems as discussed above, such as the bevel surface of the needle, i.e. the surface of the distal end is not perpendicular to the longitudinal axis of the needle (this bevel surface is not shown in FIG. 3). A further concern is how ultrasonic acoustic waves that impinge on needle 70 at a broad range of angles can be efficiently directed towards the sensing surface of the transducer.

Figure 14:
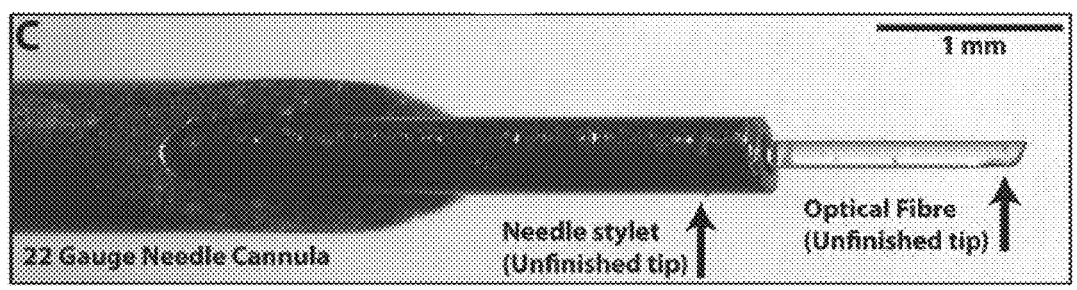
FIG. 14 is a photograph of a needle having a cannula incorporating a stylet which in turn incorporates an optical fiber (the tip of this needle is not completed).
Figure 15:
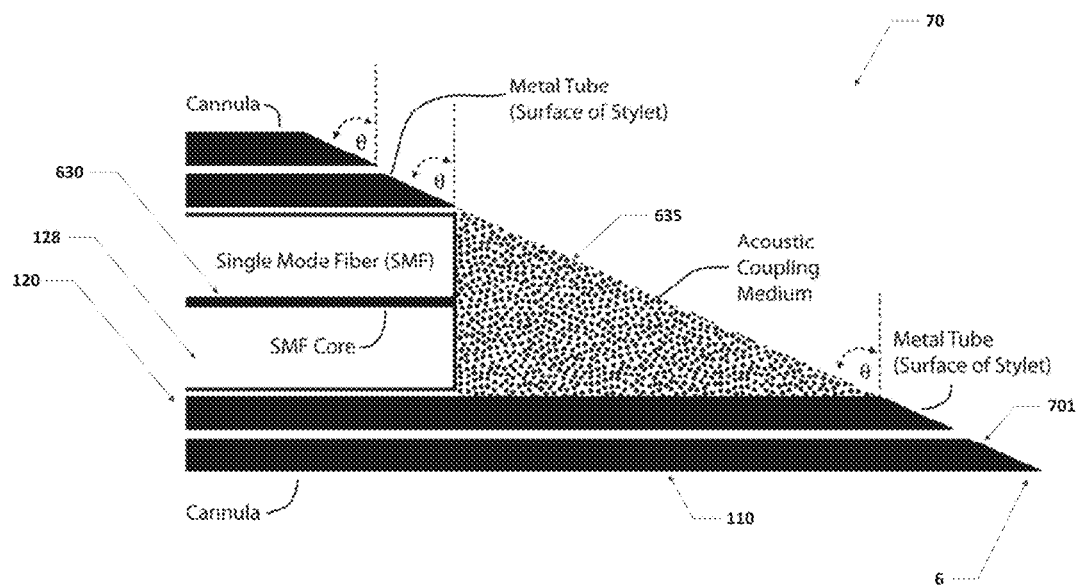
FIG. 15 is a schematic diagram (longitudinal cross-section) of a needle having the same general structure as shown in FIG. 14, including a completed tip, in accordance with one embodiment of the invention.

FIG. 14 is a photograph of one embodiment of a needle having a cannula incorporating a stylet, which in turn incorporates an optical fiber (the tip of this needle is not completed). The line representing 1 mm (top right) is indicative of the sizing that can be achieved. FIG. 15 is a schematic diagram showing a needle 70 having the same structure as the needle of FIG. 14, but with a completed tip 6 that includes a transducer 123. The tip of the needle has an oblique cut (bevel) with respect to the longitudinal (axial) direction of the needle. The needle 70 comprises a cannula 110, which surrounds a metal tube forming the outer surface of the stylet 120. Included within the stylet, and running the length of the stylet, is an optical fiber 128, in particular, a single mode fiber (SMF) having a central SMF core 630. (Other embodiments may use a double-clad fiber instead of an SMF fiber).

In one embodiment, the optical fiber has a thickness (diameter) of approximately 125 µm. The optical fiber 128 may be a single mode fiber, a double clad fiber, or any other suitable device to act as light guide. The optical fiber 128 is used in effect to carry two optical signals—the first can be considered as an incident or interrogation light signal, while the second is a reflected light signal from the distal end of the needle 70. This reflected light signal is affected (modulated) by the ultrasound signal impinging on the needle 70. When the reflected light signal is passed from the optical fiber to a suitable transceiver 205, the received ultrasound acoustic signal can be recovered from these modulations of the reflected light signal.

In the embodiment of FIG. 15, an acoustic coupling medium 635 that is also an optical scattering medium is placed at the end of the stylet to couple an ultrasound signal arriving at the needle tip 6 to the end of the optical fiber 128, which acts as an ultrasound sensor (optical hydrophone)—i.e. as transducer 123. Note that neither the optical fiber 128 nor the acoustic coupling medium 635 extends beyond the bevel surface 701 of the needle 70. The acoustic coupling medium has an acoustic impedance which is similar to that of typical tissue across a broad range of ultrasound frequencies (typically 0.5-20 MHz)—for example, the acoustic coupling medium may comprise silicone. The acoustic coupling medium may include optical scattering material (such as titanium dioxide, nanoparticles, etc.), and/or the acoustic coupling medium itself may perform acoustic scattering. In operation, the incoming ultrasound waves cause movement of the acoustic coupling medium, which therefore causes movement of the optical scattering material. Light from the distal end of the optical fiber (which is transparent) enters the acoustic coupling medium 635, and some of this light is reflected back into the optical fiber 128 by the optical scattering of the acoustic coupling medium. The movement of the optical scattering material is in effect encoded into the reflected optical signal, which allows the ultrasound acoustic signal incident on the acoustic coupling medium to be recovered.

Figure 16:
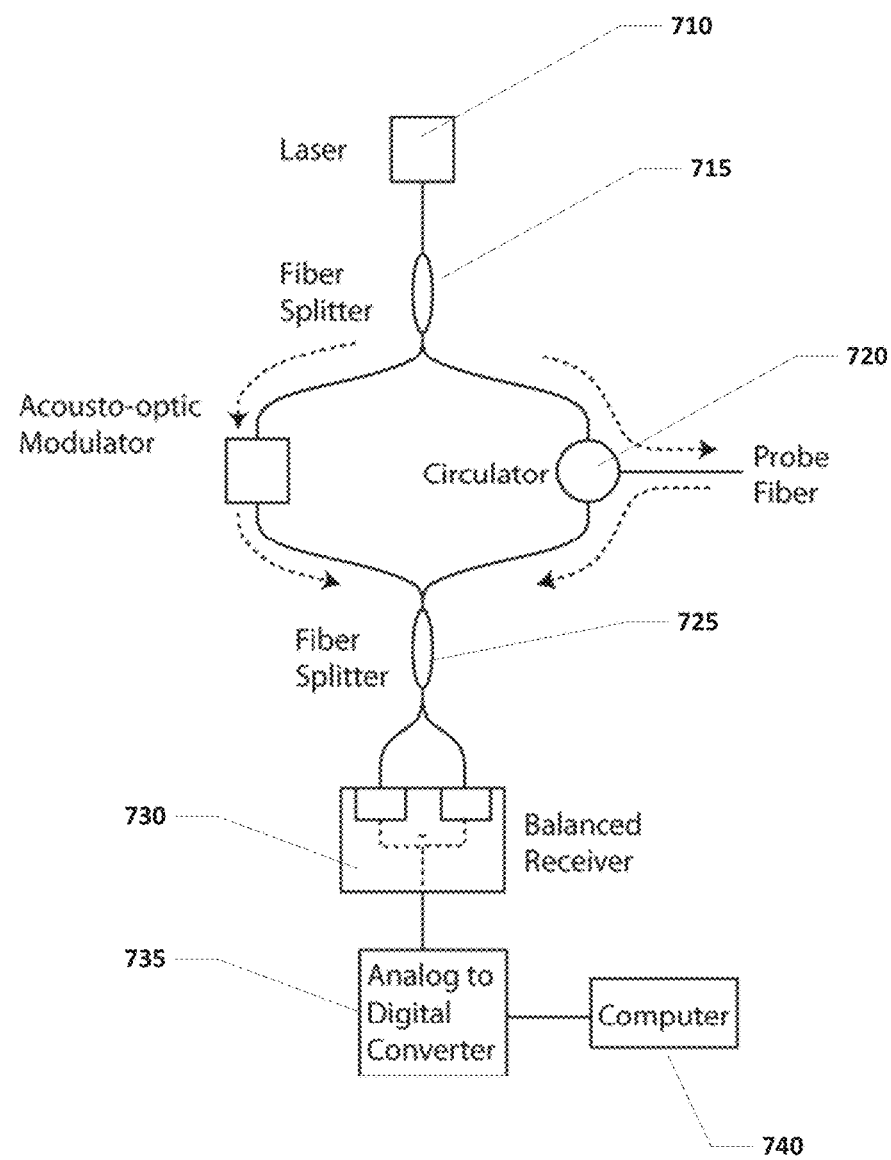
FIG. 16 is an interferometry system to support the operation of the needle transducer shown in FIG. 15 in accordance with one embodiment of the invention.

FIG. 16 illustrates an interferometry system to support the operation of a needle transducer such as shown in FIG. 15. (Note that a somewhat similar system is described by Carp et al in Applied Physics Letters, 85(3) pp. 5772-5774 for detecting the displacement of a tissue surface due to the propagation of acoustic waves). In this system, a laser 710 generates light which passes through a fiber splitter 715. One portion of the light is passed via a circulator into the optical fiber 128 of needle 70 to travel to the end of the optical fiber at needle tip 6. This light portion is then reflected back to the circulator 720, and travels from there to another fiber splitter 725. The other portion of light from fiber splitter 715 arrives at fiber splitter 725 via an acousto-optic modulator. The two signals from fiber splitter 725 are combined in balanced receiver 730, and the resulting signal is passed through analog-to-digital convertor 735 for analysis by computer 740. The apparatus shown in FIG. 16 uses interferometry to detect a phase shift between the light reflected from the tip of the needle (in particular from acoustic coupling medium 635 and the interrogation light source that passes through acousto-optic modulator 730. This phase shift then allows the ultrasound acoustic modulation incident on the acoustic coupling medium 635 to be determined.

Figure 17:
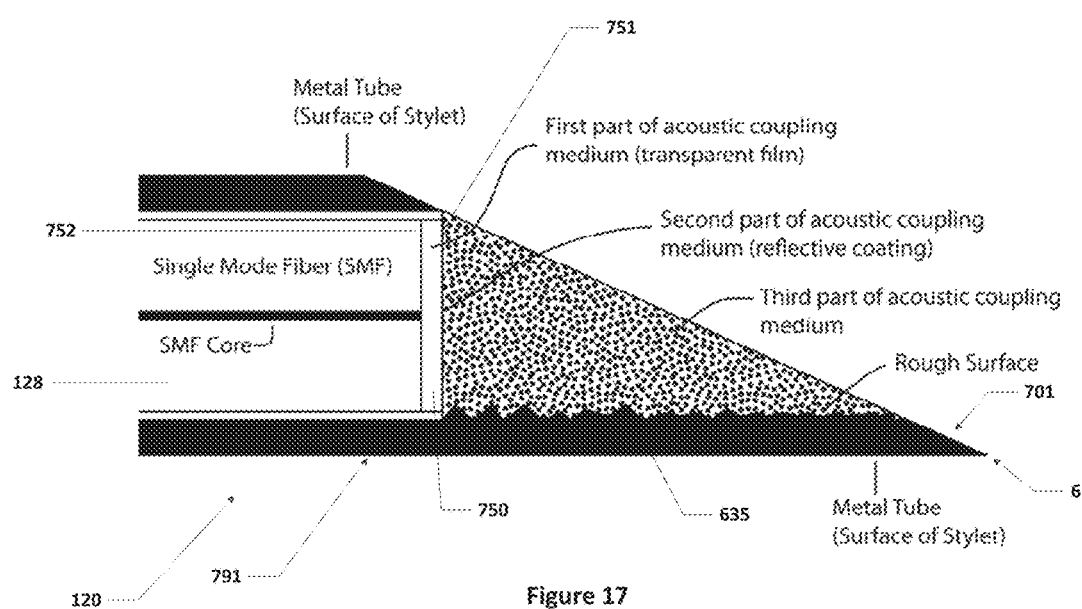
FIG. 17 is a schematic diagram (longitudinal cross-section) of a needle stylet having a transducer incorporated therein in accordance with one embodiment of the invention.

FIG. 17 illustrates a needle stylet 120 in accordance with one embodiment of the invention. The stylet comprises an outer, tubular metal wall 791, and an optical fiber 128 located in and running the central lumen of the stylet 120. The end of the optical fiber is provided with a spacer coating 750, approximately 10 μm in thickness (measured in the axial direction), and made, for example, of polyimide, PDMS (polydimethylsiloxane), or Parylene (poly-para-xylylene). Again, neither the optical fiber 128 nor the acoustic coupling medium 635 (if it is provided) extends beyond the bevel surface 701 of the needle stylet 120. The inner surface of outer, tubular metal wall 791 is roughened for enhanced echogenicity.

Incident light is passed along the optical fiber 128 to the distal end of the needle stylet 120 corresponding to tip 6. The distal end of the optical fiber includes a first (proximal) reflective coating 752 that is partly optically transparent. The light (partly) passes through this film into spacer coating 750, which is provided with a second optically reflective coating 751 at its distal end. Accordingly, a Fabry-Perot cavity is formed at the distal end face of the optical fiber between the first reflective coating 752 and the second reflective coating 751. Ultrasound acoustic waves propagate through the acoustic coupling medium result (via the acoustic coupling medium 635, if provided) to the Fabry-Perot cavity. As the light is reflected from the Fabry perot cavity, the intensity of the reflected light is dependent on (modulated by) the thickness of the spacer coating 750, which in turn varies according to the ultrasound signal that is received (e.g. via the acoustic coupling medium 635 if it is provided). The reflected light is then passed back along the optical fiber 128 within needle 70 for receipt and analysis by console 65.

Figure 14A:
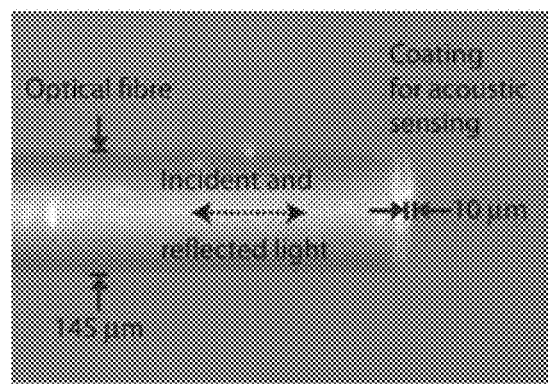
FIG. 14A is a photograph of an optical fibre which can be incorporated into the medical instrument of FIG. 2 in accordance with one embodiment of the invention.

FIG. 14A is a photograph of one embodiment of an optical fibre 128 such as used in the instrument of FIG. 17, showing in particular the polymer spacing coating at the end of the optical fiber. It will be appreciated that the dimensions specified in FIG. 14A (and also in FIG. 14) are by way of example only, and may vary from one embodiment to another. Further details about using an optical fiber such as shown in FIGS. 17 and 14A as an ultrasound sensor can be found in Beard P et al, IEEE Transactions on Ultrasonics, Ferroelectrics and Frequency Control, v47(1): 256-264, and Morris P et al, J. Acoust. Soc. Am., 2009; 125(6): 3611-3622.

Figure 17A:
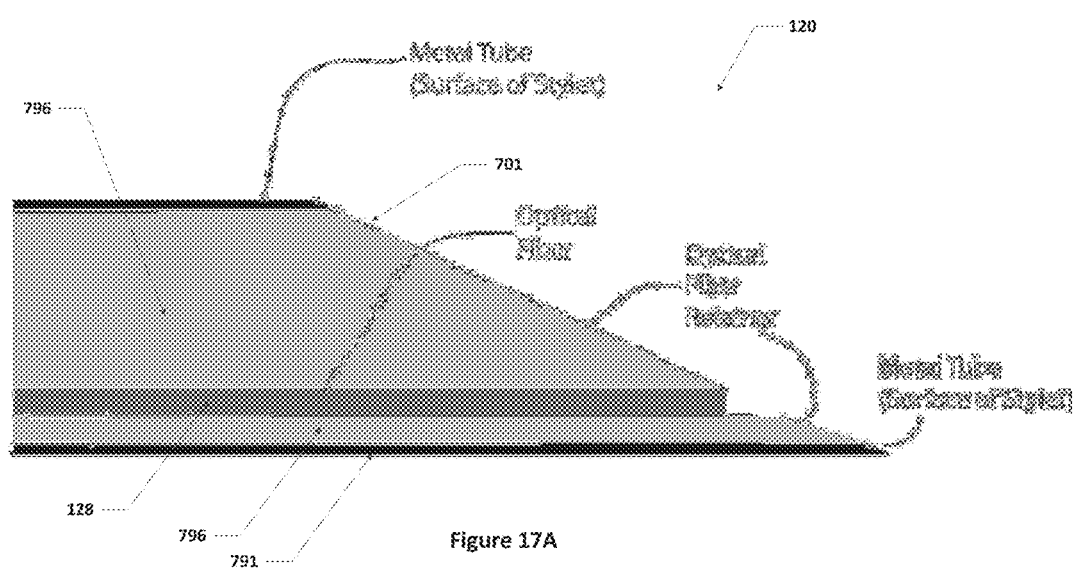
FIG. 17A is a schematic diagram (longitudinal cross-section) of a needle stylet having a transducer incorporated therein in accordance with another embodiment of the invention.

FIG. 17A is a longitudinal cross-section of a needle stylet 120 in accordance with another embodiment of the invention. This stylet may be utilised in a medical instrument 70, such as by incorporating with a cannula 110 to form a needle 70 (analogous to the configuration shown in FIG. 15). The stylet includes a retainer 796, which may be made for example of plastic or metal, to hold an optical fiber 128 in position relative to the stylet. This retainer extends at least the distal portion of the stylet 120 and includes occupies an inner channel or lumen of the stylet, formed within the outer metal tubular wall 791 of the stylet to run in a longitudinal direction along the stylet. The retainer itself includes an inner channel or lumen running in a longitudinal direction along the stylet, with the optical fiber 128 being held within this channel. Note that the optical fiber does not extend past the bevelled surface 701 of the stylet. The optical fiber 128 may be a single mode or double clad fiber, or any other suitable device, and is configured to act as a transducer for detecting ultrasound transmissions. For example, the optical fiber may be provided with a spacing coating and reflective layers in substantially the same manner as described above in relation to FIG. 17 (except that the optical fiber 128 in the embodiment of FIG. 17A receives the ultrasound transmissions propagating within the patient body directly, without any acoustic coupling material 635).

Some embodiments may use a Fiber Bragg Grating for the transducer 123 instead of forming a Fabry-Perot cavity. Another possibility is to provide an optical scattering medium at the distal end of the instrument. This can produce interference between light reflected from the distal end of the optical fiber 128 and the light back-coupled into the fiber from the scattering medium. The interference is then modulated by the incident ultrasonic energy (which causes motion within the optical scattering medium). The light source may provide light which is intensity, phase or frequency modulated, and/or comprises at least two wavelengths. Another possibility is that the optical hydrophone comprises an optical fiber with at least two reflective surfaces at the distal end. These two reflective surfaces are separated by a medium, such as a gas, having a low elastic modulus between the reflective surfaces. This causes interference of light between the reflective surfaces to be modulated by incident ultrasonic energy, and hence allows the transducer to detect such incoming ultrasonic transmissions.

The proximal end of the optical fiber 128, at the opposite end of the needle tip, may have a bifurcation (not shown in FIG. 17) into at least two smaller fibers. One of these smaller fibers is used to deliver light to the distal end of the medical instrument 70, while the second smaller fiber is used to receive light from the distal end of the medical instrument. The bifurcated region may have a coating with a refractive index that is matched (substantially similar) to the cladding of the optical fiber in the non-bifurcated region. Such a configuration can also be used with other forms of optical light guide instead of optical fiber 128, for example, a polymer light guide.

Figure 18A:
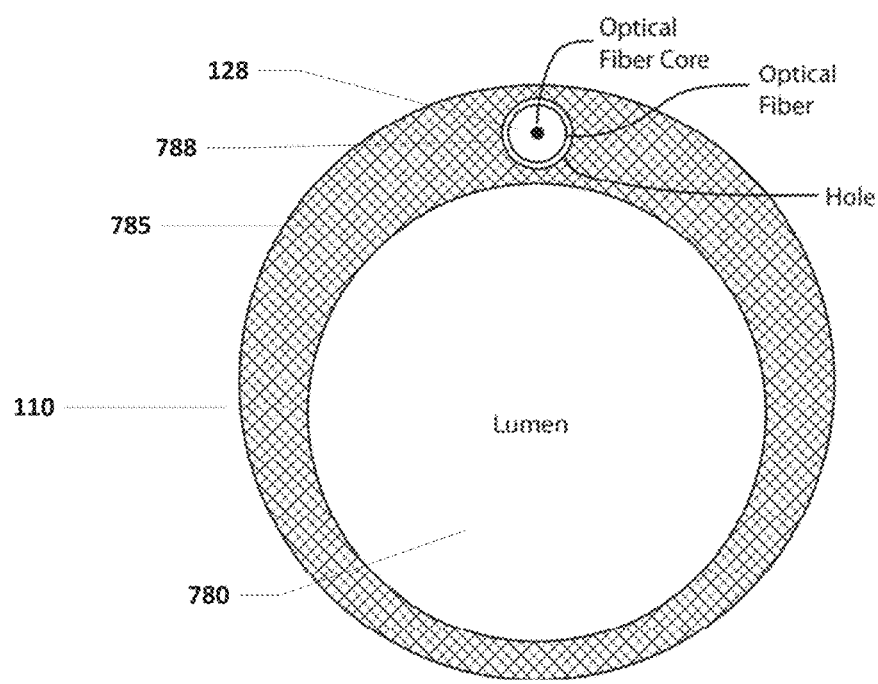
FIGS. 18A and 18B illustrate in schematic form a transducer incorporated into a needle cannula in accordance with one embodiment of the invention, where
Figure 18B:
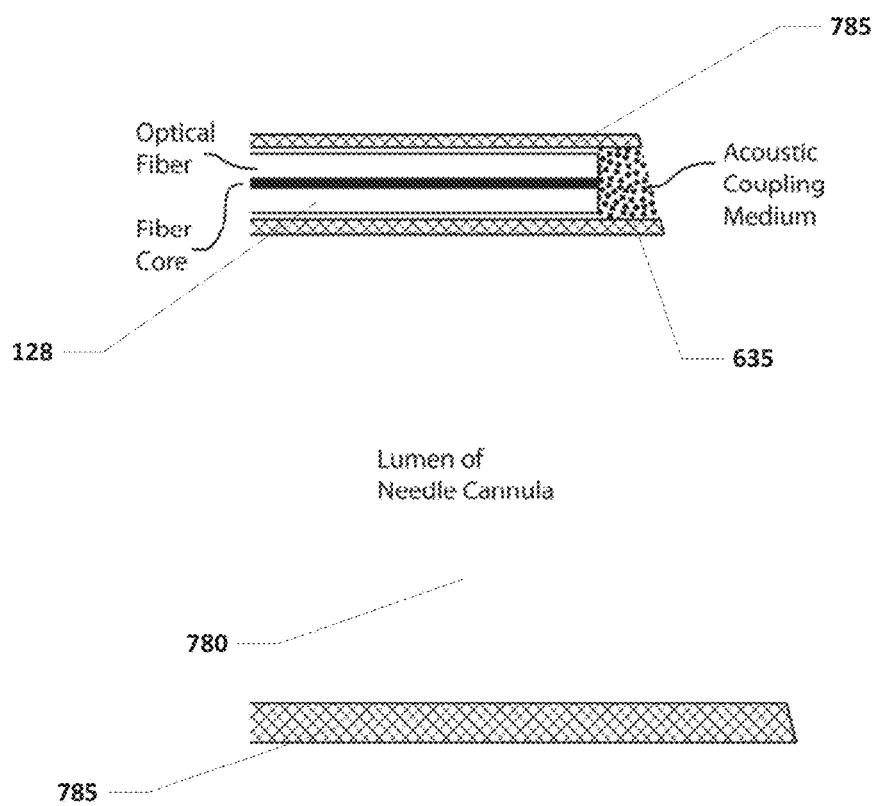

The above embodiments have integrated the transducer 123 into stylet 120. However, in other embodiments, the transducer may be integrated into the cannula 110, as shown in FIGS. 18A and 18B. In particular, FIG. 18A presents a cross-section of a cannula perpendicular to the longitudinal (axial) direction, showing a central lumen 780, for example for injecting fluids (or for receiving stylet 120), where lumen 780 is surrounded by wall 785. The optical fiber 128 of the transducer 123 is passed through (along) an internal hole 788 running along the length of wall 785. This configuration is also illustrated in FIG. 18B, which is a cross-section parallel to the longitudinal (axial) direction.

Figure 19A:
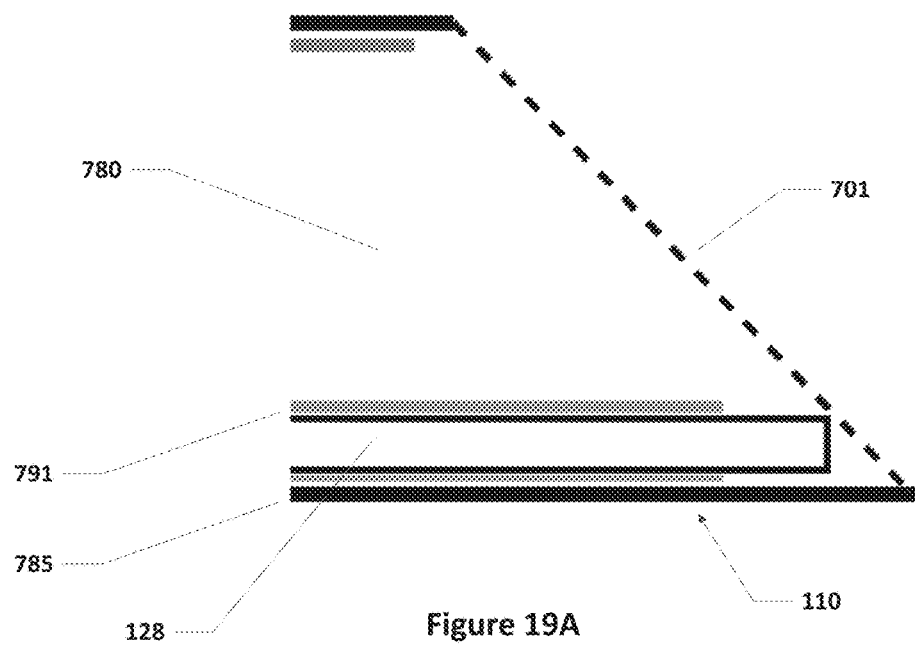
FIGS. 19A and 19B illustrate in schematic form a transducer incorporated into a needle cannula in accordance with another embodiment of the invention, where
Figure 19B:
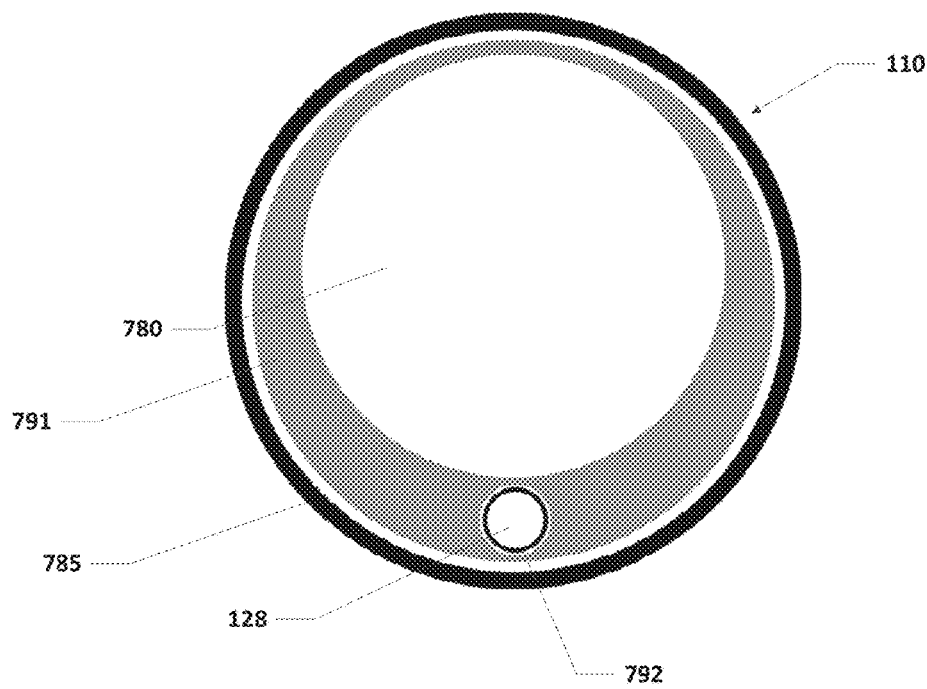

FIGS. 19A and 19B are a modification of the embodiment of FIGS. 18A and 18B, with FIG. 19A again showing a transverse cross-section of cannula 110, while FIG. 19B shows a longitudinal cross-section. In this embodiment, the lumen 780 of the cannula is provided with a sheath 791, for example, made of plastic. The sheath generally hugs the inner surface of the outer wall 785 of the cannula (the gap shown in FIG. 19 between the sheath 791 and wall 785 is for clarity only). At least one portion of the sheath is thick enough to include a second hole or lumen 792, in which optical fiber 128 is located to run along the length of the cannula. Note that again the optical fiber 128 does not extend past the bevelled surface 701.

Figure 20A:
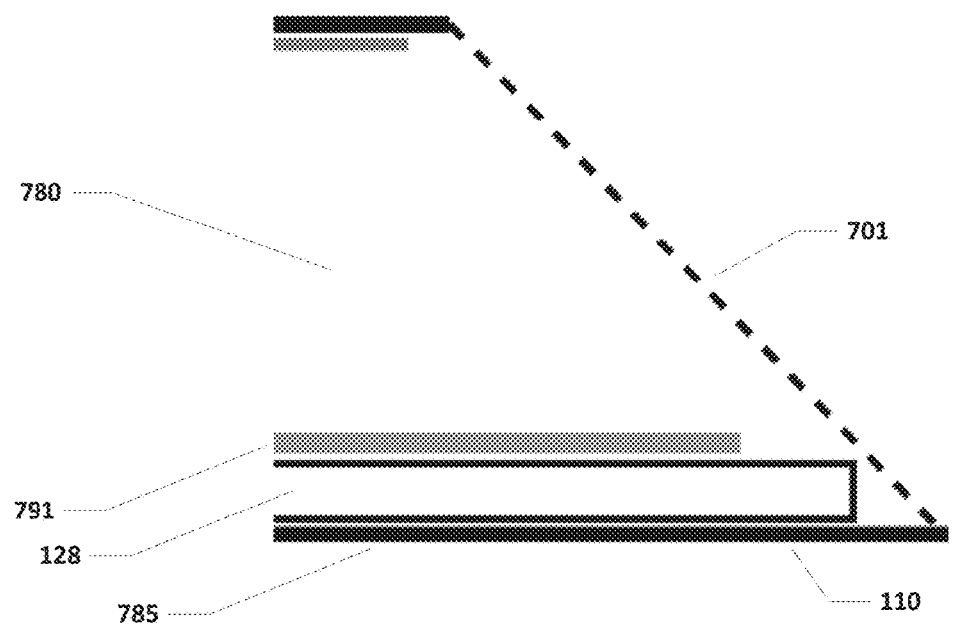
FIGS. 20A and 20B illustrate in schematic form a transducer incorporated into a needle cannula in accordance with another embodiment of the invention, where
Figure 20B:
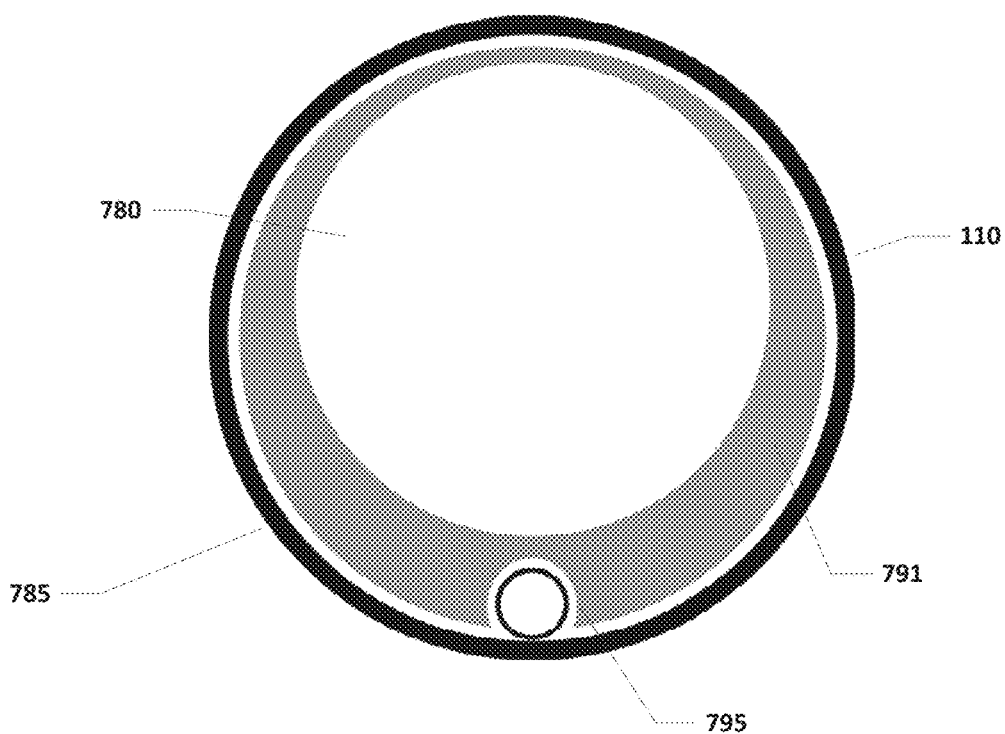

FIG. 19 is another modification of the embodiment of FIG. 18, with FIG. 20A again showing a transverse cross-section of cannula 110, while FIG. 20B shows a longitudinal cross-section. The lumen 780 of the cannula is provided with a sheath 791, for example, made of plastic. The sheath generally hugs the inner surface of the outer wall 785 of the cannula (the gap shown in FIG. 20A between the sheath 791 and wall 785 is for clarity only). The sheath includes a groove or indentation 795 to accommodate the optical fiber 128, which runs along the length of the cannula. Note that again the optical fiber 128 does not extend past the bevelled surface 701. In some implementations, a groove, indentation, or other form of locating structure may be provided on the inner surface of the cannula wall 785 to retain the optical fiber in position (this may be provided instead of or in addition to a groove or similar structure 795 in the sheath 791). In some implementations, the sheath may be flexible and resilient enough to distort around the optical fiber 128 to retain it in position relative to the cannula wall 785, without their being any groove or similar structure 795 in the sheath 791. In these implementations, some form of retaining structure may be provided on the inner surface of the cannula wall 785. This then helps to retain the optical fiber 128 in a fixed position inside the cannula, and also to reduce any distortion of the lumen 780 within the sheath 790. If distal portions of the optical fiber 128 are integrated into the needle cannula, proximal portions of this optical fiber may be directed through tubing that is connected to the proximal end of the optical fiber and used for injections (e.g. by connecting the tubing to syringes) before connection at the console 65.

Figure 20C:
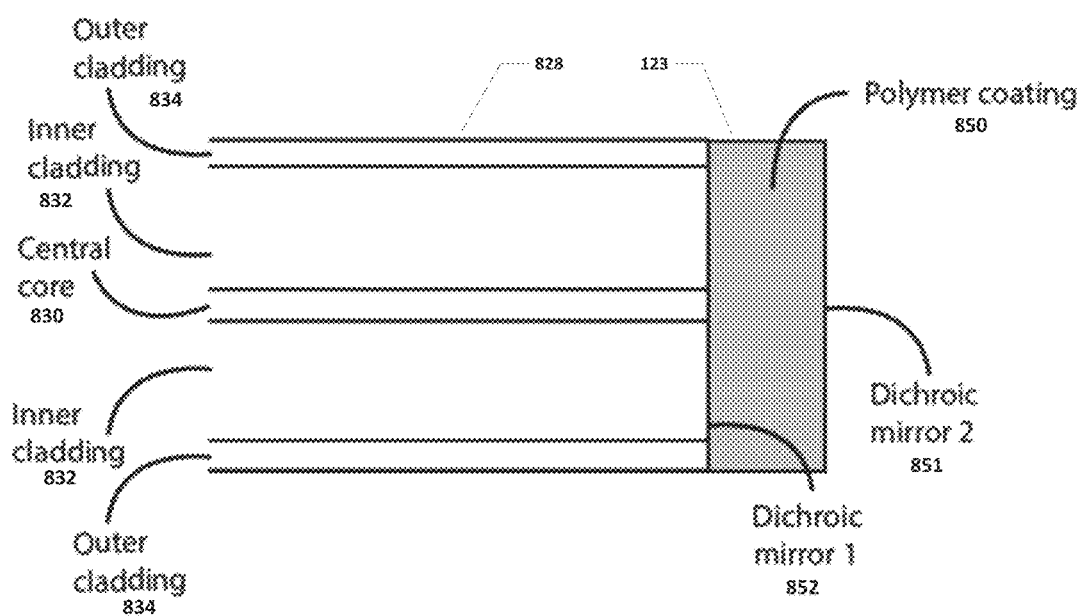
FIG. 20C is a schematic diagram of an optical fibre which can be incorporated into a medical instrument, for example, the medical instrument shown in FIG. 2, in accordance with some embodiments of the invention.

In some embodiments, the optical fiber 128 is a double-clad optical fibre as illustrated in FIG. 20C, which has a central core 830 for transmitting single-mode light, an inner cladding 832, and an outer cladding 834. By way of example, the central core 830 may have an outer diameter of 9 μm, the inner cladding may have an outer diameter of 105 μm, and the outer cladding may have outer diameters of 125 μm. It will be appreciated that these measurements are by way of illustration only, and different embodiments may have different measurements. For example, in some embodiments, the outer diameter of the inner cladding will be in the range 5-20 μm, the outer diameter of the inner cladding will be in the range of 50-150 μm, and the outer diameter of the outer cladding will be in the range 80-200 μm. Again, it will be appreciated that these measurements are by way of illustration only, and different embodiments may have different measurements.

At the distal end face of the double-clad optical fiber 128, a cavity is formed between a first dichroic coating 851 and a second dichroic coating 852. For example, there could be a polymer spacer or coating 850 between the two dichroic coatings 851, 852. These dichroic coatings substantially reflect light in a first wavelength range, i.e. they act as mirrors for light in the first wavelength range, and substantially transmit light in a second wavelength range (different from the first wavelength range). Note that the second wavelength range may be contiguous or non-contiguous (e.g. split into two portions, one or either side of the first wavelength range).

For light in the first wavelength range, the cavity formed by the polymer coating 850 and the two dichroic coatings 851, 852 forms a Fabry-Perot etalon, which is configured to act as an ultrasound sensor as described above. In other words, the Fabry-Perot etalon comprising the polymer coating 850 and the two dichroic coatings 851, 852 forms part of transducer 123 for converting an incoming ultrasound signal arriving at the tip of the medical instrument into a data signal imposed on interrogation light in the first wavelength range which impinges on the Fabry-Perot etalon.

In contrast, light in the second wavelength range may be transmitted through the polymer coating 850 and the two dichroic coatings 851, 852, out of the optical fibre 128 and into tissue; conversely, light in the second wavelength range may also be received from tissue through the polymer coating 850 and the two dichroic coatings 851, 852 into the optical fibre 128.

In some embodiments, the central core 830 and the inner cladding 832 of a double-clad fiber are accessed using a power combiner (not shown). Using the multi-mode inputs of a power combiner, light in the second wavelength range may be delivered to and received from the double-clad fibre (for instance, using a separate console); using the single-mode input of a power combiner, light in the first wavelength range can be delivered to and received from the central core 830.

Figure 20D:
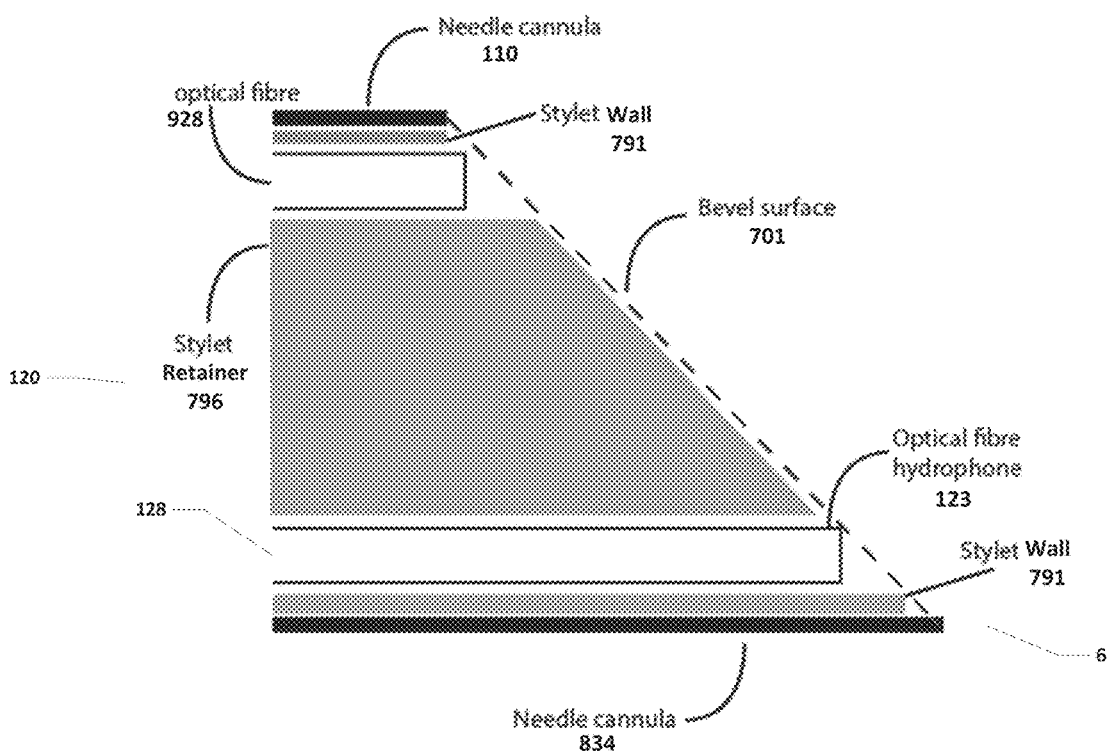
FIG. 20D is a schematic illustration of the optical fiber of FIG. 20C incorporated into a needle stylet in accordance with some embodiments of the invention.
Figure 20E:
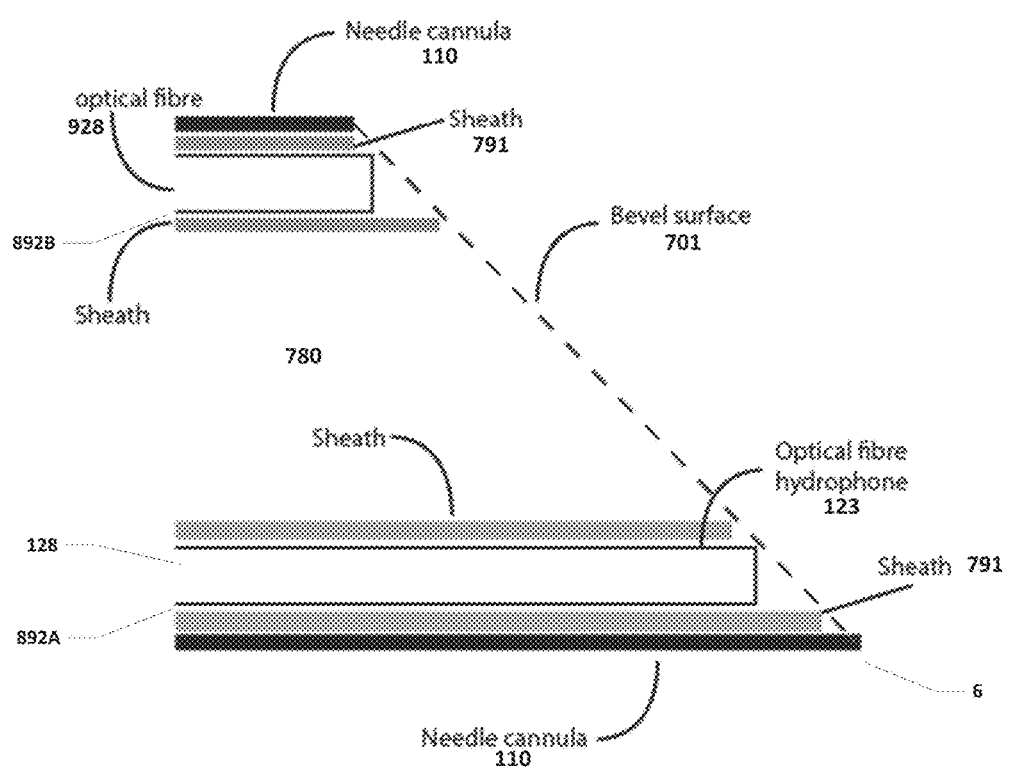
FIG. 20E is a schematic illustration of the optical fiber of FIG. 20C incorporated into a needle cannula in accordance with some embodiments of the invention.

FIGS. 20D and 20E show two embodiments in which a double-clad fiber 128, such as shown in FIG. 20C, is supplemented by at least one additional optical fibre 928. The end of the optical fibre 128 is fitted with an optical hydrophone (transducer 123) for detecting incoming ultrasound transmissions. (In both FIG. 20D and 20E, the double-clad fiber 128 is located in portion of the needle tip which extends further out, by virtue of bevel surface 701, than the portion accommodating the additional optical fibre 928; however, these positions could be reversed or otherwise modified in other embodiments). The purpose and use of this additional optical fibre 928 is described below.

FIG. 20D shows a needle cannula 834 including a stylet 120. Analogous to the stylet shown in FIG. 17A, the stylet comprises an outer wall 791, generally cylindrical in shape, and a retainer 796 that holds the two optical fibres 128, 928 in position in the stylet. FIG. 20E shows a needle cannula 110 that includes a sheath 791 to accommodate the optical fibre 128 and the additional optical fibre 928 (analogous to FIGS. 19A and 19B). In particular, the sheath 791 includes a central (open or vacant) lumen 780, plus two smaller lumens 892A, 892B to accommodate optical fibres 892A and 892B respectively. It will be appreciated that other aspects of the embodiments of FIGS. 20D and 20E may be formed as described elsewhere herein, for example as regards the presence of an acoustic scattering medium, such as shown in FIG. 17. Conversely, a dichroic mirror such as shown in FIG. 20C may be incorporated into other embodiments of medical instruments described herein (not just those shown in FIGS. 20D and 20E).

In the embodiments of FIGS. 20C, 20D and 20E, light may be provided into tissue to obtain information using a variety of different sensing modalities. For example, light may be transmitted along the optical fibre 128 out through the dichroic mirror into tissue and/or along one or more additional optical fibres, such as fibre 928, 892A, 892B. Similarly, any light which is then received from the tissue for use in the sensing may be received into optical fibre 128 through the dichroic mirror and/or into one or more additional optical fibres, such as fibre 928, 892A, 892B, and then fed into an appropriate apparatus for analysis, e.g. a spectrometer. By way of example, light having the second wavelength range may be provided into tissue through the optical fibre 128, including the dichroic mirror, and may then be scattered. A portion of this scattered light may be received by the additional fiber(s) 928 and/or by the double clad fiber itself to obtain a measurement of reflectance. As another example, light provided into tissue may be absorbed and then generate fluorescence, with this fluorescent light subsequently being received by one or more additional optical fibers 928 that are integrated into the needle. In other embodiments, the additional fibre may be omitted, in which case the light may be provided to tissue using the single mode core 830, and received back from tissue via the outer cladding 834.

Irrespective of whether or not the incoming light is received into the same optical fibre 128 as provided with transducer 123, in both cases light received from tissue may be spectroscopically resolved. For example, a spectrometer could be used to resolve received light into different wavelength components, or a light source in which wavelengths are encoded with different modulation frequencies or codes could be used in conjunction with the demodulation of signals from a photodetector.

Signals obtained from the detection of received scattered light may be processed using an inversion model to obtain information about intrinsic tissue chromophores, such as hemoglobin, deoxy-hemoglobin, water, lipid, bilirubin, or cytochrome c, extrinsic chromophores, such as indocyanine green (ICG), and the effective scattering coefficient. Similarly, signals obtained from the detection of received fluorescent light may be processed to obtain information about intrinsic tissue fluorophores such as collagen, flavin-adenine dinucleotide (FAD), and nicotinamide adenine dinucleotide (NADH).

Another possibility is that light provided into tissue can generate ultrasound when it is absorbed in tissue—this is known as the photoacoustic effect. Photoacoustic ultrasound resulting from such a procedure may be received using the Fabry-Perot etalon on the double-clad fiber 128 and/or with an external ultrasound transducer, such as one positioned on the surface of the body.

A device such as shown in FIGS. 20C, 20D and 20E can thus be used to provide a medical instrument having a needle-like shape for insertion into a human body. Such an instrument comprises an elongated structure forming said needle-like shape and has a bevelled surface 701 at its distal tip. At least one optical fiber 128 runs along the elongated structure for transmitting an interrogation light signal to the distal tip and for transmitting a data signal back from the distal tip. A transducer 123 located at the distal tip detects ultrasound transmissions incident upon the distal tip or side aperture. The transducer includes at least one surface to reflect the interrogation light signal from the optical fiber with an intensity and/or phase that varies according to the incident ultrasound transmissions to generate the data signal. The at least one reflective surface which reflects the interrogation light signal is dichroic so as to be substantially reflective for light having a first wavelength range and substantially transmissive for light having a second wavelength range which is different from the first wavelength range, where the interrogation light signal falls substantially within the first wavelength range.

In some implementations, the first wavelength range comprises at least a portion of the wavelength range 400-1300 nm, and the second wavelength range comprises at least a portion of the wavelength range 1400-1600 nm (generally considered to be infrared). However, it will be appreciated that other implementations may use different wavelength ranges.

Although the above embodiments have shown the acoustic signal being received into the transducer 123 via the tip 6 of the needle or other instrument 70, the acoustic signal could also be received via a side aperture, for example, in the outer wall 785 of a cannula Such a configuration may make it easier to perform a desired medical function at the tip of the needle. Assuming that the side aperture is located at or near the tip of the medical instrument, this side aperture transducer still provides a good indication of the location of the tip of the needle based on the localisation transmissions.

In some embodiments, the medical instrument may be provided with two or more transducers, for example, one at the distal end of the medical instrument, such as shown in FIG. 3, and the other part-way along the medical instrument (which may obtain its signal via a side aperture). It will be appreciated that for a generally linear instrument, such as a needle, obtaining the spatial position of two separated (and known) points on the instrument fully specifies the location and orientation of the needle in three-dimensional space. Note that both points may be located along the need from the distal tip 6 if so desired (since the position of the tip 6 can then be directly calculated once the locations of the two points have been determined).

As described herein, ultrasound device tracking (UDT) can be used to determine the position of an interventional instrument in the human body using an ultrasound imaging probe 55. The interventional instrument, such as a needle or catheter, may include a second transducer which is a hydrophone that responds to ultrasound waves incident on its surface or on tissue close to its surface by producing a signal The probe 55 generates imaging and localisation transmissions from different (respective) sets of array elements, such that the imaging and localisation transmissions may be performed concurrently, and processes the signal received by the instrument transducer during the transmissions to determine the position of the interventional instrument within the human body. In some embodiments, the instrument transducer is incorporated into a multi-lumen polymer structure that has at least one hole suitable for fluid injections. A physical connection to the instrument transducer, such as an optical fiber, is provided through another hole of the multi-lumen polymer structure. The instrument transducer may be located at an acoustically transparent hole in the wall of the medical instrument.

From the standpoint of clinical adoption, one attractive aspect of UDT is that such device tracking can be performed without any changes to current clinical workflow. In particular, UDT helps to improve guidance of ultrasound-guided minimally invasive procedures and to reduce positional uncertainty in a manner that is compatible with current clinical workflow. The adoption of UDT will help to produce reductions in:

1) the risk of complications that arise when the position of a device tip is incorrectly identified, and a critical structure such as a blood vessel, nerve, or lung is punctured.
2) the amount of procedure time that is spent on re-orientation of the ultrasound transducer and the medical device in order to identify the position of the device tip—this leads to greater efficiency and cost savings for the hospital.
3) the time required for physicians to become proficient with ultrasound image guidance, which will lead to increased adoption of ultrasound image guidance and decreased training costs.

UDT is especially suited for use in the field of anaesthesia, such as for peripheral nerve blocks and central venous catheterisations. Additional fields of use for UDT include interventional pain management, interventional oncology, and interventional cardiology.

Overall, UDT helps to provide accurate, quantitative tracking with minimal changes to current clinical workflow, and has many advantages compared with existing approaches, including:
1. explicit tracking of the medical device position relative to the ultrasound imaging plane;
2. tracking can be performed even when the medical device is outside the ultrasound imaging plane;
3. tracking does not introduce image artifacts;
4. compatibility with devices with low echogenicity;
5. compatibility with small needles that are used frequently in clinical practice;
6. medical device construction involves disposable, low-cost, non-toxic components;
7. no pre-procedural calibrations by physicians are required (a significant advantage relative to EM tracking solutions).

The approach described herein also provides an acoustic sensor integrated into a medical needle. In one embodiment, the acoustic sensor includes at least one optical fiber integrated into the stylet and/or the cannula of the needle, so that an optical console that can deliver light to the fiber from an interrogation light source and can receive reflected light from the distal end of the fiber. A spacer coating with reflective coatings on its proximal and distal surfaces may be positioned at the distal end of the fiber to form a Fabry-Perot cavity in which there is interference between light reflected from the two reflective coatings. Light is reflected from the Fabry-Perot cavity back along the fiber, where it is propagated to a detector for processing in order to determine the intensity and phase of acoustic waves incident on the acoustic coupling medium.

Figure 21:
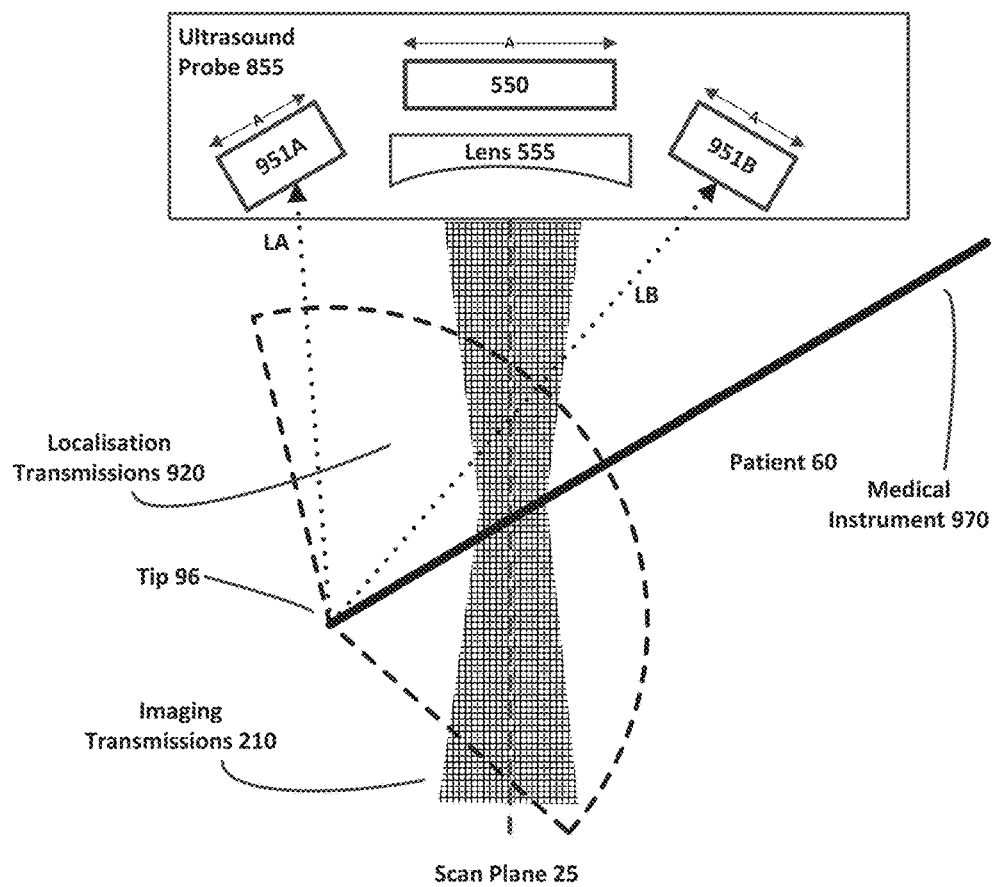
FIG. 21 illustrates another embodiment of the invention in which the localisation transmissions are produced by the medical instrument and received by the ultrasound probe.

Although various embodiments of the invention have been described above by way of example, the skilled person will be aware of many possible modifications with respect to the above embodiments. For example, although the described embodiments have primarily relied upon timing information for specific (combinations of) wavefronts or pulses to determine location, phase information across a range of wavefronts could be used instead or as well as the timing information. In some embodiments, for example, movement of the medical instrument transducer 123 could be detected from a change in phase (e.g. Doppler shift) of the incoming ultrasound signal transmissions that are extended in time. This in turn can support localisation, firstly because the signals from different localisation transducer elements experience different phase shifts, depending on the current location and angle of movement with respect to any given localisation transducer. Furthermore, information about the movement also provides predictive information with respect to a future location of the transducer or information about the orientation of the distal end of the medical instrument, as discussed above. In addition, although the embodiments described above have concentrated on receipt by the instrument transducer 123 of transmissions from the localisation transducer elements 551, the instrument transducer 123 may also receive or detect transmissions from the imaging transducer elements 550 (in addition to the localisation transmissions). In some cases, the transmissions received from the imaging transducer elements may just be the normal imaging ultrasound transmissions. In other cases, the imaging transducer elements may also be able to produce localisation ultrasound transmissions, for example, interspersed with the imaging transmissions. In the case of the imaging transducer elements producing localisation ultrasound transmissions, the ultrasound probe 55 is not expected to receive reflections of these transmissions for forming an (anatomical or structured) ultrasound image (in contrast to the situation for the conventional imaging ultrasound transmission elements). Note that any localisation ultrasound transmissions from the imaging transducer elements tend to be relatively confined or focussed to the image scan plane compared with the transmissions from the localisation transducer elements (unless the focussing of the image transducer elements can be temporarily disabled). Thus in general, it is expected that having the instrument transducer detect ultrasound transmissions (whether localisation or imaging) from the imaging transducer elements 550 will provide positional information to supplement the positional information obtained from the localisation transmissions from the dedicated localisation transducer elements 551. Nevertheless, having the instrument transducer detect ultrasound transmissions (whether localisation or imaging) from the imaging transducer elements can make a valuable contribution to the positional determination, not least because the imaging transducer elements tend to be more focussed (and hence might provide better information on depth within a body). Furthermore, the different spatial arrangement of the imaging transducer elements (compared with the localisation transducer elements) provides the potential for a wider range of signal travel time measurements, which should improve the overall accuracy of the position determination FIG. 21 illustrates another embodiment of the invention, in which the general configuration of the apparatus is similar to that of FIGS. 2, 4 and 12 (for example), except that the localisation transmissions are produced by the medical instrument 970 and received by the ultrasound probe 855 (rather than vice versa). In other words, FIG. 21 depicts a form of reverse architecture, in which the localisation transmissions go in the opposite direction to that of the previously described embodiments.

More particularly, FIG. 21 depicts a medical instrument 970 inserted into a patient body 60. At the tip 96 of the medical instrument, a transducer (not shown) is located, which emits the ultrasound localisation transmissions 920. The pattern of the localisation transmissions 920 is shown schematically by the dashed line in FIG. 21, and may comprise a low-directional (or omni-directional) signal. An example of a medical instrument which has a transducer at the tip to transmit omni-directional ultrasound signals is disclosed in U.S. Pat. No. 4,249,539.

FIG. 21 indicates two specific directions of localisation transmissions (within the broader range of transmissions) by dotted arrows LA and LB. The localisation transmissions corresponding to arrows LA and LB impinge upon, and are detected by, the localisation transducers 951A and 951B respectively within ultrasound probe 855. Thus localisation transducers 951A and 951B of ultrasound probe 855 are configured to receive the localisation transmissions (rather than to transmit the localisation transmissions as per the above embodiments). Note that the imaging transducers 550 in the ultrasound probe 855 can be the same as previously described, namely they are able to generate imaging transmissions 220 within scan plane 25 and also to receive back reflections of such imaging transmissions. The imaging transducers may also be configured to receive the localisation transmissions, provided there is no interference between the signals (which can be helped by a suitable selection of relative timing, frequency, etc., as discussed above).

The embodiment of FIG. 21 can use time of flight information, as described above, to determine the position of the needle tip 96 in the direction perpendicular to the scan plane 25 (parallel to the z axis). For example, arrows LA and LB indicate ultrasound transmissions from the needle tip 96 to localisation transducers 951A and 951B respectively. The different lengths of these arrows correspond to a different time-of-flight for the ultrasound signals, which can then be used to determine the location of the needle tip 96, following the procedure illustrated in FIG. 7. The accuracy of this measurement can again be enhanced by having the localisation transducers positioned at a number of locations along the z-axis (as shown in FIG. 13B). Similarly, a position along the x-axis (parallel to the main axis S-S of the ultrasound probe 855) can be determined by having localisation transducers again positioned along this x-axis (as also shown in FIG. 13B).

In many aspects, the embodiment of FIG. 21 is directly analogous to that of previous embodiments, and there are many potential features in common. For example, in both cases, the position of the needle tip may be tracked over time, and this historical information may then be used to supplement the most recent positional information. One difference is that the embodiment of FIG. 21 has only a single source of the localisation signal(s), namely the tip of needle 970. Consequently, there is no need for different codes or sequential transmissions (for example) to allow a receiver to distinguish between signals from different transducer elements (such as illustrated in FIG. 9). Instead, the console is connected so as to be able to determine directly which localisation transducer receives which signal timing, and to process the received signals accordingly to perform the localisation.

It will be appreciated that the various approaches described herein, e.g. where ultrasound localisation signals are transmitted from the ultrasound probe to the medical instrument (or vice versa), allow the position of the medical instrument to be directly determined in relation to the image scan plane of the ultrasound system based on the received localisation signals. This does not involve the use of separate sensors or other apparatus to determine a patient reference frame, which might then be used to locate both the image scan plane and the instrument position. Accordingly, the various approaches described herein avoid the cost and additional effort associated with providing, positioning and utilising any such separate sensors or apparatus, as well as simplifying the subsequent signal processing.

The above embodiments rely on various processing, such as analysing the received signals to determination a position of the medical instrument, which may be performed by specialised hardware, by general purpose hardware running appropriate computer code, or by some combination of the two. For example, the general purpose hardware may comprise a personal computer, a computer workstation, etc. The computer code may comprise computer program instructions that are executed by one or more processors to perform the desired operations. The one or more processors may be located in or integrated into special purpose apparatus, such as an ultrasound system. The one or more processors may comprise digital signal processors, graphics processing units, central processing units, or any other suitable device. The computer program code is generally stored in a non-transitory medium such as an optical disk, flash memory (ROM), or hard drive, and then loaded into random access memory (RAM) prior to access by the one or more processors for execution.

In conclusion, the skilled person will be aware of various modifications that can be made to the above embodiments to reflect the particular circumstances of any given implementation. Moreover, the skilled person will be aware that features from different embodiments can be combined as appropriate in any given implementation. Accordingly, the scope of the present invention is defined by the appended claims and their equivalents.

Various embodiments of the invention are defined in the following numbered clauses:

1. An ultrasound probe for acquiring an anatomical image of a human body and for locating a medical instrument with respect to said image, the ultrasound probe including a first set of imaging transducer elements and a second set of localisation transducer elements, wherein the first set of imaging transducer elements are distinct and disjoint from the second set of localisation transducer elements, wherein:
   the first set of imaging transducer elements are configured to: (i) produce ultrasound imaging transmissions into the human body, wherein the ultrasound imaging transmissions are focussed into an image scan plane, and (ii) receive reflections of the ultrasound imaging transmissions for generating a two-dimensional anatomical image corresponding to the image scan plane; and
   the second set of localisation transducer elements are configured to produce ultrasound localisation transmissions into the human body for locating the medical instrument with respect to the anatomical image, wherein the ultrasound localisation transmissions extend outside the image scan plane, and wherein at least two transducer elements from said second set are spaced from one other in a direction perpendicular to the image scan plane.
2. The ultrasound probe of clause 1, wherein the imaging transducer elements in the first set have at least one lens to focus the imaging transmissions into the image scan plane.
3. The ultrasound probe of clause 2, wherein the localisation transducer elements in the second set either do not have a lens or have at least one lens which has or is controlled to have different focussing properties from the at least one lens of the imaging transducer elements in the first set.
4. The ultrasound lens probe of any preceding clause, wherein the imaging transducer elements in the first set can also be configured to produce ultrasound localisation transmissions.
5. The ultrasound probe of any preceding clause, wherein at least one imaging transducer element in the first set is structurally distinct from at least one localisation transducer element in the second set.
6. The ultrasound probe of clause 5, wherein at least one imaging transducer element in the first set has a different curvature from at least one localisation transducer element in the second set.
7. The ultrasound probe of clause 5 or 6, wherein at least one imaging transducer element in the first set has a different orientation from at least one localisation transducer element in the second set.
8. The ultrasound probe of any preceding clause, wherein the imaging transducer elements in the first set are arranged in a different geometrical pattern or configuration from the localisation transducer elements in the second set.
9. The ultrasound probe of clause 8, wherein the imaging transducer elements in the first set form a row, and the localisation transducer elements in the second set comprise at least one pair of rows, with each pair having one row on each side of and parallel to the row of the first set of transducer elements.
10. The ultrasound probe of clause 9, wherein there are at least two adjacent rows on each side of and parallel to the row of the first set of transducer elements, and elements in one row of said at least two adjacent rows are structurally distinct from elements in an adjacent row.

11. The ultrasound probe of any preceding clause, wherein the ultrasound imaging transmissions are produced at substantially the same time as the ultrasound localisation transmissions.

12. The ultrasound probe of clause 11, wherein the ultrasound imaging transmissions are produced simultaneously with the ultrasound localisation transmissions.

13. The ultrasound probe of clause 11, wherein ultrasound imaging transmissions are repeatedly interspersed with the ultrasound localisation transmissions.

14. The ultrasound probe of any preceding clause, wherein said ultrasound localisation transmissions are varied according to one or more previously determined locations and/or the currently predicted location of the medical instrument.

15. The ultrasound probe of clause 14, wherein said ultrasound localisation transmissions are varied in intensity.

16. The ultrasound probe of any preceding clause, wherein said ultrasound localisation transmissions are electronically focussed using phased array principles.

17. The ultrasound probe of clause 16, wherein the localisation transmissions are electronically focussed in a plane that is substantially parallel to the image scan plane and unfocussed in a plane that is substantially perpendicular to the image scan place.

18. The ultrasound probe of clause 16 or 17, wherein the localisation transmissions are focussed to a different depth from the imaging transmissions.

19. The ultrasound probe of any of clauses 16 to 18, wherein there is a sequence of localisation transmissions with different spatial positions for the electronic focussing.

20. The ultrasound probe of any of clauses 16 to 19, wherein there is a sequence of localisation transmissions comprising ultrasound beams directed at different angles.

21. The ultrasound probe of any preceding clause, wherein the ultrasound localisation transmissions are arranged to produce an ultrasound signal having a temporal structure that varies with position.

22. The ultrasound probe of clause 21, wherein the ultrasound localisation transmissions comprise successive wavefronts that are steered in different directions.

23. The ultrasound probe of any preceding clause, wherein different transducer elements or groups of transducer elements in said second set of localisation transducer elements are configured to transmit localisation transmissions in a predetermined sequence.

24. The ultrasound probe of any preceding clause, wherein a localisation transmission comprises a chirp.

25. The ultrasound probe of any preceding clause, wherein a localisation transmission comprises a sequence of pulses.

26. The ultrasound probe of clause 25, wherein the sequence of pulses has low autocorrelation properties.

27. The ultrasound probe of any preceding clause, wherein different transducer elements or groups of transducer elements in said second set of localisation transducer elements are configured to transmit individually identifiable localisation transmissions in substantially the same or overlapping time periods.

28. The ultrasound probe of clause 27, wherein the individually identifiable localisation transmissions incorporate different signal sequences.

29. The ultrasound probe of clause 28, wherein the individually identifiable localisation transmissions incorporate different signal sequences that have low cross-correlation properties.

30. The ultrasound probe of any preceding clause, wherein a localisation transmission comprises phase modulations of a carrier frequency.

31. The ultrasound probe of any preceding clause, wherein the frequency of the imaging transmissions is different from the frequency of the localisation transmissions.

32. The ultrasound probe of any preceding clause, wherein localisation transmissions from a first group of localisation transducer elements are electronically focussed to a first spatial location, and localisation transmissions from a second group of localisation transducer elements are electronically focussed to a second spatial location, wherein the first spatial location is distinct and separate from the second spatial location, and wherein the localisation transmissions from the first group may be simultaneous with the localisation transmissions from the second group.

33. The ultrasound probe of any preceding clause, wherein localisation transmissions from a first group of localisation transducer elements are electronically focussed to a first spatial location, and imaging transmissions from a second group of imaging transducer elements are electronically focussed to a second spatial location, wherein the first spatial location is distinct and separate from the second spatial location, wherein the localisation transmissions from the first group may be simultaneous with the localisation transmissions from the second group.

34. A medical instrument having a needle-like shape for insertion into a human body, said instrument comprising:
an elongated structure forming said needle-like shape and having a bevelled surface at its distal tip;
at least one optical fiber, running along the elongated structure, for transmitting an interrogation light signal to the distal tip and for transmitting a data signal back from the distal tip;
a transducer located at the distal tip for detecting ultrasound transmissions incident upon the distal tip or side aperture, wherein the transducer includes at least one surface to reflect the interrogation light signal from the optical fiber with an intensity and/or phase that varies according to the incident ultrasound transmissions to generate said data signal, wherein the transducer does not extend beyond said bevelled surface.

35. The medical instrument of clause 34, wherein the transducer includes two reflective surfaces that form a Fabry-Perot cavity for the interrogation light signal.

36. The medical instrument of clause 34 or 35, wherein the optical fiber is a single-mode optical fiber with a cladding diameter in the range of 50 to 125 microns.

37. The medical instrument of any of clauses 34 to 36, wherein the distal tip of the at least one optical fiber or a part of the needle adjacent to the distal tip of the at least one optical fiber is further provided with an acoustic scattering medium to scatter the incident ultrasound transmissions onto the transducer, wherein said acoustic scattering medium does not extend beyond said bevelled surface.

38. The medical instrument of any of clauses 34 to 37, wherein said at least one optical fiber is incorporated into a needle stylet.

39. The medical instrument of any of clauses 34 to 37, wherein said at least one optical fiber is incorporated into a needle cannula, said cannula comprising an outer wall having an inner surface defining an internal lumen, and a sheath generally adjacent to a part of the inner surface, wherein the optical fiber is positioned in said internal lumen, either inside a lumen in said sheath or between the inner surface and said sheath 40. The medical instrument of clause 39, wherein the inner surface of the outer wall of the cannula is provided with at a groove on said inner surface, and wherein the optical fiber is retained within said groove.

41. The medical instrument of clause 39 or 40, wherein there is at least one side aperture at or adjacent to the distal end of the cannula that allows incident ultrasound transmissions to reach the transducer.

42. An ultrasound system comprising:
   an ultrasound unit including an ultrasound probe as defined in any of clauses 1 to 33 for producing said ultrasound localisation transmissions into a human body, wherein said ultrasound localisation transmissions are received by the transducer in a medical instrument; and
   a sensor console for receiving the signals from said transducer that correspond to localisation transmissions;
   wherein the received signals are processed by the ultrasound system to determine the location of the medical instrument within the human body relative to the ultrasound probe.

43. The ultrasound system of clause 42, wherein the ultrasound unit further comprises a display device for displaying an image corresponding to the image scan plane, together with an indication of the determined location of the medical instrument relative to the image scan plane.

44. The ultrasound system of clause 42 or 43, wherein the sensor console is configured to receive information about the localisation transmissions produced by the ultrasound probe.

45. The ultrasound system of clause 44, wherein said information comprises information about the timing of said localisation transmissions produced by the ultrasound probe.

46. The ultrasound system of clause 45, wherein the sensor console uses said timing information to determine ultrasound propagation times of the localisation transmissions from the ultrasound probe to the transducer in the medical instrument, wherein said ultrasound propagation times are used to determine the location of the medical instrument.

47. The ultrasound system of any of clauses 42 to 46, wherein at least one the sensor console and the ultrasound unit processes the received localisation transmissions in conjunction with one or more previously determined locations of the medical instrument to determine an updated location of the medical instrument within the human body relative to the ultrasound probe.

48. The ultrasound system of clause 47, wherein a currently determined location is processed in conjunction with one or more previously determined locations of the medical instrument to determine a trajectory of the medical instrument within the human body relative to the ultrasound probe for display by the ultrasound unit.

49. The ultrasound system of any of clauses 42 to 48, wherein each of the sensor console and the ultrasound unit has a clock, and wherein said ultrasound system is able to synchronise said clocks.

50. The ultrasound system of any of clauses 42 to 49, further comprising a first connection from the ultrasound unit to the sensor console for providing a trigger signal at the start of the ultrasound localisation transmissions, and a second connection from the sensor console to the ultrasound unit for providing information derived from the signals received by the transducer in the medical instrument.

51. The ultrasound system of any of clauses 42 to 50, wherein the signals received by the transducer in the medical instrument are cross-correlated with signal patterns known to be generated by different localisation transducer elements in the ultrasound probe in order to determine ultrasound propagation times of the localisation transmissions from the ultrasound probe to the transducer in the medical instrument.

52. The ultrasound system of clause 51, wherein said signal pattern is derived from one or more signals received from the transducer in the medical instrument.

53. The ultrasound system of any of clauses 42 to 52, wherein said medical instrument is as specified in any of clauses 42 to 52.

54. A method of using an ultrasound probe for acquiring an anatomical image of a human body and for locating a medical instrument with respect to said image, the ultrasound probe including a first set of imaging transducer elements and a second set of localisation transducer elements, wherein the first set of imaging transducer elements are distinct and disjoint from the second set of localisation transducer elements, the method comprising:
   the first set of imaging transducer elements producing ultrasound imaging transmissions into the human body, wherein the ultrasound imaging transmissions are focussed into an image scan plane, and receiving reflections of the ultrasound imaging transmissions for generating a two-dimensional anatomical image corresponding to the image scan plane; and
   the second set of localisation transducer elements producing ultrasound localisation transmissions into the human body for locating the medical instrument with respect to the anatomical image, wherein the ultrasound localisation transmissions extend outside the image scan plane;
   wherein at least two transducer elements from said second set are spaced from one other in a direction perpendicular to the image scan plane.

55. The method of clause 54, further comprising:
   receiving said ultrasound localisation transmissions by a transducer in the medical instrument;
   receiving by a sensor console the signals from said transducer that correspond to localisation transmissions; and
   processing the received signals to determine the location of the medical instrument within the human body relative to the ultrasound probe.

56. An ultrasound probe for acquiring an anatomical image of a human body and for locating a medical instrument with respect to said image, the ultrasound probe including a first set of imaging transducer elements and a second set of localisation transducer elements, wherein the first set of imaging transducer elements are distinct and disjoint from the second set of localisation transducer elements, wherein:
   the first set of imaging transducer elements are configured to: (i) produce ultrasound imaging transmissions into the human body, wherein the ultrasound imaging transmissions are focussed into an image scan plane, and (ii) receive reflections of the ultrasound imaging transmissions for generating a two-dimensional anatomical image corresponding to the image scan plane; and
   the second set of localisation transducer elements are configured to receive ultrasound localisation transmissions for locating the medical instrument with respect to the anatomical image, wherein the ultrasound localisation transmissions are produced by the medical instrument and travel to the localisation transducer elements through the human body, and wherein at least two transducer elements from said second set are spaced from one other in a direction perpendicular to the image scan plane so as to receive the ultrasound localisation transmissions from spatial regions of the human body which extend beyond the image scan plane.

57. An ultrasound system comprising:
an ultrasound unit including an ultrasound probe as defined in clause 56 for receiving said ultrasound localisation transmissions, wherein said ultrasound localisation transmissions are produced by a transducer in a the medical instrument; and
a sensor console for receiving the signals from said ultrasound unit that correspond to localisation transmissions;
wherein the received signals are processed by the ultrasound system to determine the location of the medical instrument within the human body relative to the ultrasound probe.

58. A method of operating an ultrasound probe for acquiring an anatomical image of a human body and for locating a medical instrument with respect to said image, the ultrasound probe including a first set of imaging transducer elements and a second set of localisation transducer elements, wherein the first set of imaging transducer elements are distinct and disjoint from the second set of localisation transducer elements, wherein the method comprises:
the first set of imaging transducer elements producing ultrasound imaging transmissions into the human body, wherein the ultrasound imaging transmissions are focussed into an image scan plane, and receiving reflections of the ultrasound imaging transmissions for generating a two-dimensional anatomical image corresponding to the image scan plane; and
the second set of localisation transducer elements receiving ultrasound localisation transmissions for locating the medical instrument with respect to the anatomical image, wherein the ultrasound localisation transmissions are produced by the medical instrument and travel to the localisation transducer elements through the human body;
and wherein at least two transducer elements from said second set are spaced from one other in a direction perpendicular to the image scan plane so as to receive the ultrasound localisation transmissions from spatial regions of the human body which extend beyond the image scan plane.

59. The method of clause 58, wherein an ultrasound unit including said ultrasound probe which receives said ultrasound localisation transmissions, the method further comprising:
a sensor console receiving signals from said ultrasound unit that correspond to the localisation transmissions; and
processing the received signals to determine the location of the medical instrument within the human body relative to the ultrasound probe.

What is claimed is:

1. An ultrasound system comprising:
an ultrasound unit including an ultrasound probe for acquiring an anatomical image of a human body and for locating a medical instrument with respect to said anatomical image, the ultrasound probe including a first set of imaging transducer elements and a second set of localisation transducer elements, wherein the first set of imaging transducer elements are distinct and disjoint from the second set of localisation transducer elements, wherein: the first set of imaging transducer elements are configured to: (i) produce ultrasound imaging transmissions into the human body, wherein the ultrasound imaging transmissions are focussed into an image scan plane, and (ii) receive reflections of the ultrasound imaging transmissions for generating a two-dimensional anatomical image corresponding to the image scan plane; and wherein the second set of localisation transducer elements are configured to produce ultrasound localisation transmissions into the human body for locating the medical instrument with respect to the two-dimensional anatomical image, wherein the ultrasound localisation transmissions extend outside the image scan plane, such that at least four localisation transducer elements from said second set are spaced from one another in a direction perpendicular to the image scan plane so as to be arranged at four or more different offsets from the image scan plane; and
a sensor console for receiving signals from a transducer that correspond to the localisation transmissions;
wherein the ultrasound system is configured to process the received signals to determine the location of the medical instrument within the human body relative to the ultrasound probe based on the received signals.

2. The ultrasound system of claim 1, wherein the imaging transducer elements in the first set have at least one lens to focus the imaging transmissions into the image scan plane.

3. The ultrasound system of claim 2, wherein the localisation transducer elements in the second set either do not have a lens or have at least one lens which has or is controlled to have different focussing properties from the at least one lens of the imaging transducer elements in the first set.

4. The ultrasound system of claim 1, wherein the imaging transducer elements in the first set can also be configured to produce ultrasound localisation transmissions.

5. The ultrasound system of claim 1, wherein at least one imaging transducer element in the first set is structurally distinct from at least one localisation transducer element in the second set.

6. The ultrasound system of claim 5, wherein at least one imaging transducer element in the first set has a different curvature from at least one localisation transducer element in the second set.

7. The ultrasound system of claim 5, wherein at least one imaging transducer element in the first set has a different orientation from at least one localisation transducer element in the second set.

8. The ultrasound system of claim 1, wherein the imaging transducer elements in the first set are arranged in a different geometrical pattern or configuration from the localisation transducer elements in the second set.

9. The ultrasound system of claim 8, wherein the imaging transducer elements in the first set form a row, and the localisation transducer elements in the second set comprise at least one pair of rows, with each pair having one row on each side of and parallel to the row of the first set of transducer elements.

10. The ultrasound system of claim 9, wherein there are at least two adjacent rows on each side of and parallel to the row of the first set of transducer elements, and elements in one row of said at least two adjacent rows are structurally distinct from elements in an adjacent row.

11. The ultrasound system of claim 1, wherein the ultrasound imaging transmissions are produced at substantially the same time as the ultrasound localisation transmissions.

12. The ultrasound system of claim 1, wherein the ultrasound imaging transmissions are repeatedly interspersed with the ultrasound localisation transmissions.

13. The ultrasound system of claim 1, wherein said ultrasound localisation transmissions are varied according to one or more previously determined locations and/or the currently determined location of the medical instrument.

14. The ultrasound system of claim 1, wherein said ultrasound localisation transmissions are electronically focussed using phased array principles.

15. The ultrasound system of claim 1, wherein different transducer elements or groups of transducer elements in said second set of localisation transducer elements are configured to transmit localisation transmissions in a predetermined sequence.

16. The ultrasound system of claim 1, wherein a localisation transmission comprises a sequence of pulses.

17. The ultrasound system of claim 16, wherein the sequence of pulses has low autocorrelation properties.

18. The ultrasound system of claim 1, wherein the frequency of the imaging transmissions is different from the frequency of the localisation transmissions.

19. The ultrasound system of claim 1, wherein the ultrasound unit further comprises a display device for displaying the two-dimensional anatomical image corresponding to the image scan plane, together with an indication of the determined location of the medical instrument relative to the image scan plane.

20. The ultrasound system of claim 1, wherein the sensor console is configured to receive information about the localisation transmissions produced by the ultrasound probe.

* * * * *